United States Patent
Hematti et al.

(10) Patent No.: US 10,563,172 B2
(45) Date of Patent: Feb. 18, 2020

(54) METHODS OF T CELL EXPANSION AND ACTIVATION

(71) Applicant: Wisconsin Alumni Research Foundation, Madison, WI (US)

(72) Inventors: Peiman Hematti, Middleton, WI (US); Debra Bloom, Sun Prairie, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/458,339

(22) Filed: Mar. 14, 2017

(65) Prior Publication Data

US 2017/0260506 A1    Sep. 14, 2017

Related U.S. Application Data

(60) Provisional application No. 62/307,989, filed on Mar. 14, 2016.

(51) Int. Cl.
| | | |
|---|---|---|
| *C12N 5/0783* | (2010.01) | |
| *A61K 39/00* | (2006.01) | |
| *A61K 9/00* | (2006.01) | |
| *A61K 35/17* | (2015.01) | |

(52) U.S. Cl.
CPC .......... *C12N 5/0638* (2013.01); *A61K 9/0019* (2013.01); *A61K 35/17* (2013.01); *A61K 39/0011* (2013.01); *A61K 2039/5158* (2013.01); *C12N 2501/50* (2013.01); *C12N 2501/515* (2013.01); *C12N 2501/599* (2013.01); *C12N 2510/00* (2013.01)

(58) Field of Classification Search
CPC ........ A61K 2039/505; A61K 39/39558; A61K 35/17; A61K 38/177; A61K 47/6849; C07K 2317/24; C07K 16/2803; C07K 14/7051; C12N 2510/00; C12N 5/0636; C12N 5/0638; C12N 2501/515; G01N 2015/0065; G01N 33/505; G01N 2015/008; G01N 33/56972
See application file for complete search history.

(56) References Cited

U.S. PATENT DOCUMENTS

2015/0352208 A1    12/2015    Fearon

FOREIGN PATENT DOCUMENTS

| WO | 01/89539 | 11/2001 |
|---|---|---|
| WO | 2001/89539 | 11/2001 |
| WO | 2015/112626 | 7/2015 |

OTHER PUBLICATIONS

Bloom, et al., 2009. BAFF is increased in renal transplant patients following treatment with alemtuzumab. Am J Transplant 9:1835-1845.
Bloom, et al., A reproducible immunopotency assay to measure mesenchymal stromal cell-mediated T-cell suppression. 2015 Cytotherapy 17:140-151.
Bossen, et al., 2006. BAFF, APRIL and their receptors: structure, function and signaling. Semin Immunol 18:263-275.
Callahan, et al., CTLA-4 and PD-1 Pathway Blockade: Combinations in the Clinic, 2014, Frontiers in oncology 4:385.
Diaz-de-Durana, et al., 2006. TACI-BLyS signaling via B-cell-dendritic cell cooperation is required for naive CD8+ T-cell priming in vivo. Blood 107:594-601.
Faurschou, et al., 2014. Anti-B cell antibody therapies for inflammatory rheumatic diseases. Annu Rev Med 65:263-278.
Figueroa, et al., 2015. Chimeric antigen receptor engineering: a right step in the evolution of adoptive cellular immunotherapy. International reviews of immunology 34:154-187.
Frigault, et al., 2015. Identification of chimeric antigen receptors that mediate constitutive or inducible proliferation of T cells. Cancer immunology research 3:356-367.
Kim, et al., 2011. Accelerated central nervous system autoimmunity in BAFF-receptor-deficient mice. J Neurol Sci 306:9-15.
Lesley, et al., 2004. Reduced competitiveness of autoantigen-engaged B cells due to increased dependence on BAFF. Immunity 20:441-453.
Ma, et al., 2008. Protein kinase C delta localizes to secretory lysosomes in CD8+ CTL and directly mediates TCR signals leading to granule exocytosis-mediated cytotoxicity. Journal of immunology (Baltimore, Md. : 1950) 181:4716-4722.
Mackay, et al., Cracking the BAFF code, Nat Rev Immunol, 2009, 9:491-502.
Mackay, et al., B cells and the BAFF/APRIL axis: fast-forward on autoimmunity and signaling. Curr Opin Immunol 2007, 19:327-336.
Ng, et al., 2004. B cell-activating factor belonging to the TNF family (BAFF)-R is the principal BAFF receptor facilitating BAFF costimulation of circulating T and B cells. Journal of immunology (Baltimore, Md. : 1950) 173:807-817.
Ninomiya, et al., 2015. Tumor indoleamine 2,3-dioxygenase (IDO) inhibits CD19-CAR T cells and is downregulated by lymphodepleting drugs. Blood 125:3905-3916.
Patino-Lopez, et al., 2006. Human class-I restricted T cell associated molecule is highly expressed in the cerebellum and is a marker for activated NKT and CD8+ T lymphocytes. Journal of neuroimmunology 171:145-155.
Ryan, et al., 2009. Targeting of BAFF and APRIL for autoimmunity and oncology. Adv Exp Med Biol 647:52-63.
Schiemann, et al., 2001. An essential role for BAFF in the normal development of B cells through a BCMA-independent pathway. Science (New York, N.Y.) 293:2111-2114.
Sutherland, et al., 2005. BAFF augments certain Th1-associated inflammatory responses. Journal of immunology (Baltimore, Md. : 1950) 174:5537-5544.
Takeuchi, et al., 2016. CRTAM determines the CD4+ cytotoxic T lymphocyte lineage. The Journal of experimental medicine 213:123-138.

(Continued)

Primary Examiner — Lynn Y Fan
(74) Attorney, Agent, or Firm — Quarles & Brady LLP

(57) ABSTRACT

The present disclosure relates to methods, cells, and compositions for preparing T cell populations and compositions for adoptive cell therapy. In particular, provided herein are methods for efficiently expanding and activating T cell populations for genetic engineering and adoptive T cell immunotherapies. Also provided are cells and compositions produced by the methods and methods of their use.

27 Claims, 17 Drawing Sheets

(56) References Cited

OTHER PUBLICATIONS

Vincent, et al., 2013. The BAFF/APRIL system: emerging functions beyond B cell biology and autoimmunity. Cytokine Growth Factor Rev 24:203-215.

Ye, et al., 2004. BAFF binding to T cell-expressed BAFF-R costimulates T cell proliferation and alloresponses. Eur J Immunol 34:2750-2759.

Stroncek, et al., Highlights of the society for immunotherapy of cancer (SITC) 27th annual meeting, Journal for Immunotherapy of Cancer, Biomed Central Ltd, London, UK, vol. 1, No. 1, May 29, 2013 (May 29, 2013), pp. 1-11.

Wang, et al., Current advances in T-cell-based cancer immunotherapy, Immunotherapy, vol. 6, No. 12, Dec. 1, 2014 (Dec. 1, 2014), pp. 1265-1278.

Mackay, et al., The role of the BAFF/APRIL system on T cell function, Seminars in Immunology, W.B. Saunders Company, PA, US, vol. 18, No. 5, Oct. 1, 2006 (Oct. 1, 2006), pp. 284-289.

International Search Report and Written Opinion from PCT/US2017/022260, dated May 31, 2017, 19 pages.

Trickett et al. "T cell stimulation and expansion using anti-CD3/CD28 beads," 2003, J. Immuno. Methods, 275:251-255.

Riddell et al. "The use of anti-CD3 and anti-CD28 monoclonal antibodies to clone and expand human antigen-specific T cells," 1990, J. Immuno. Methods, 128(2):189-207.

Sadelain et al. "The basic principles of chimeric antigen receptor design," 2013, Cancer Discovery, 388-398.

Garlie et al. "T cells coactivated with immobilized anti-CD3 and anti-CD28 as potential immunotherapy for cancer," J. Immunotherapy, 1999, 22(4):336-345.

Teschner et al. "In vitro stimulation and expansion of human tumor-reactive CD8+ cytotoxic T lymphocytes by anti-CD3/CD28/CD137 magnetic beads," Scandinavian Journal of Immunology, 2011, 74:155-164.

Li et al. "Comparison of anti-CD3 and anti-CD28-coated beads with soluble anti-CD3 for expanding human T cells: differing impact on CD8 T cell phenotype and responsiveness to restimulation," J. Trans. Med., 2010, 8:104.

Onlamoon et al. "Anti-CD3/28 mediated expansion of macaque CD4+ T cells in polyclonal and provides extended survival after adoptive transfer," J. Med. Primatol, 2007, 36:206-218.

Ghassemi et al. "Reducing ex vivo culture improves the antileukemic activity of chimeric antigen receptor (CAR) T cells," Cancer Immunology Research, 2018, 6(9).

FIGS. 3A-3C
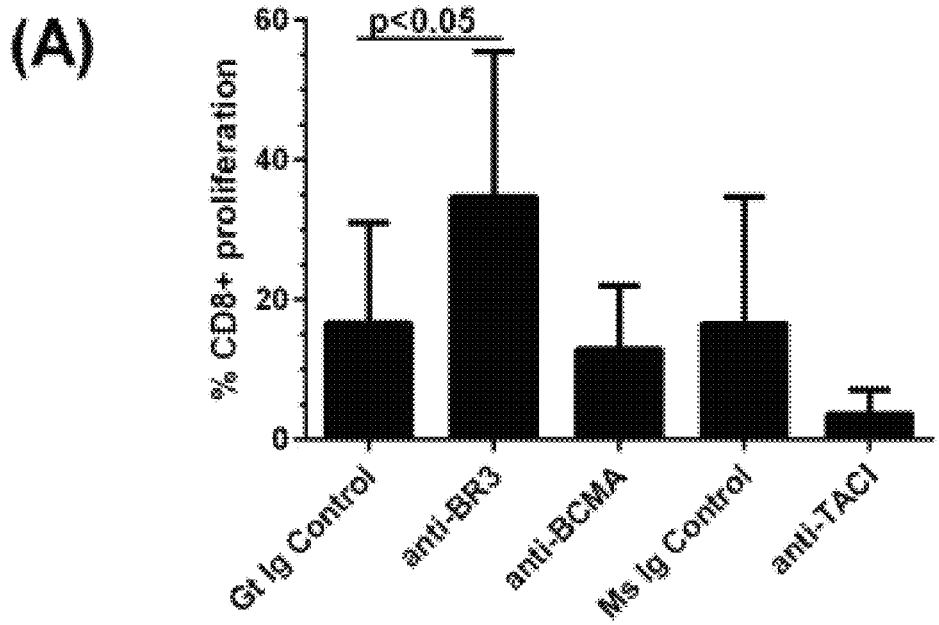
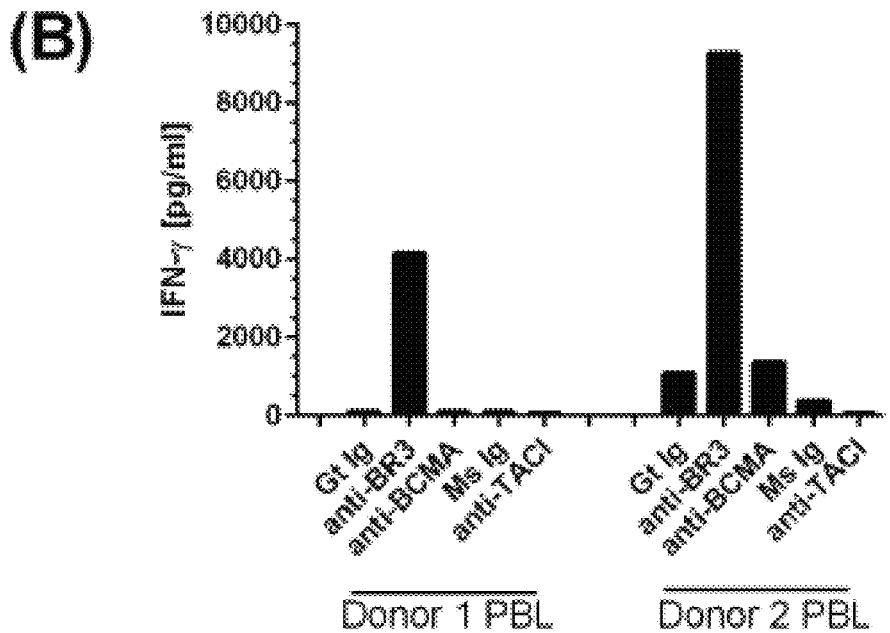

FIGS. 3A-3C, CONTINUED
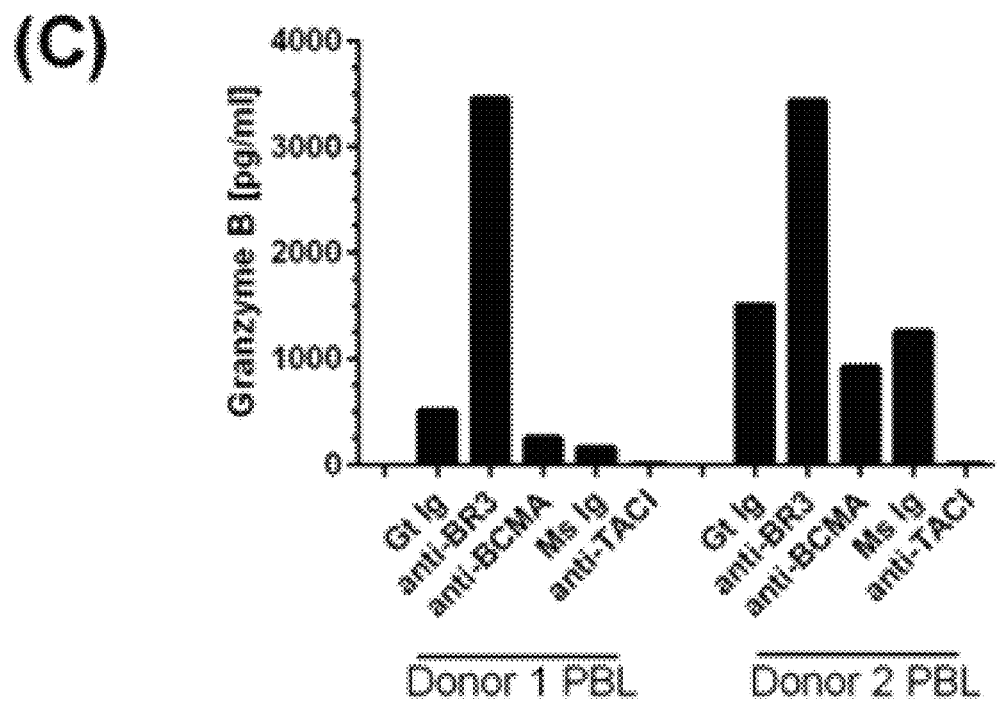

FIGS. 4A-4D
A
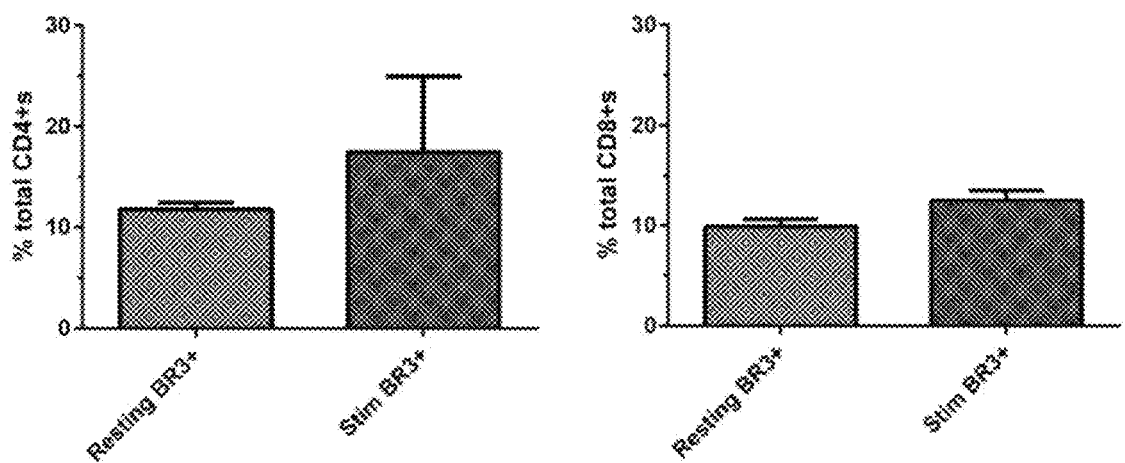
B
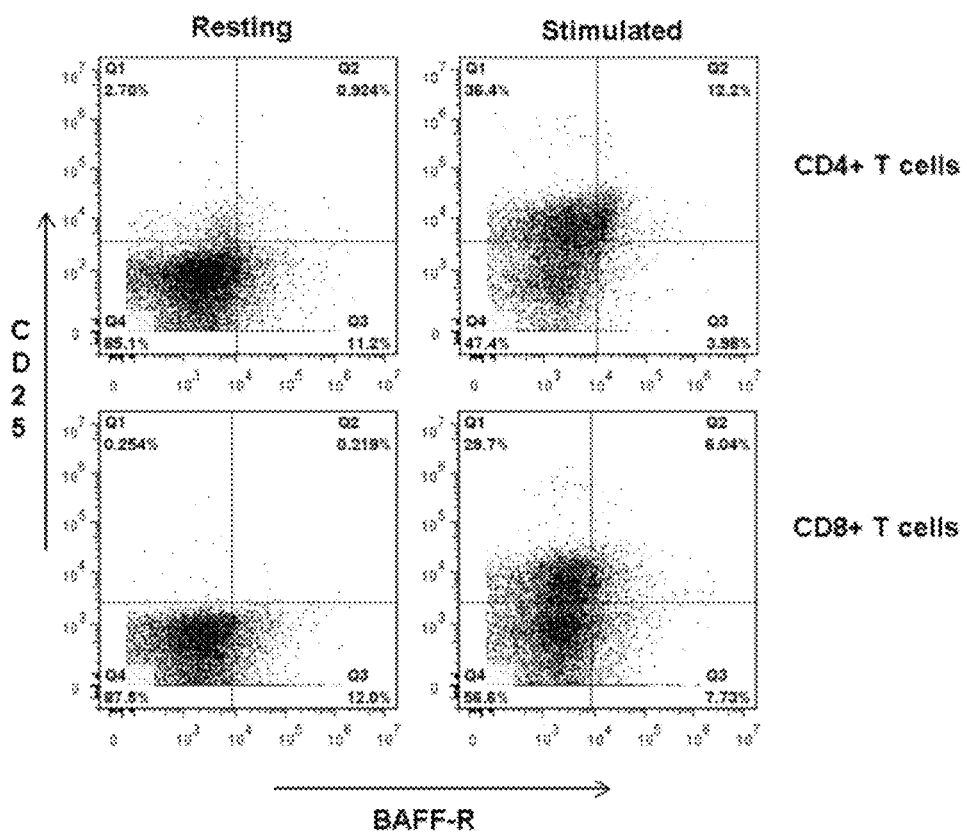

FIGS. 4A-4D (continued)
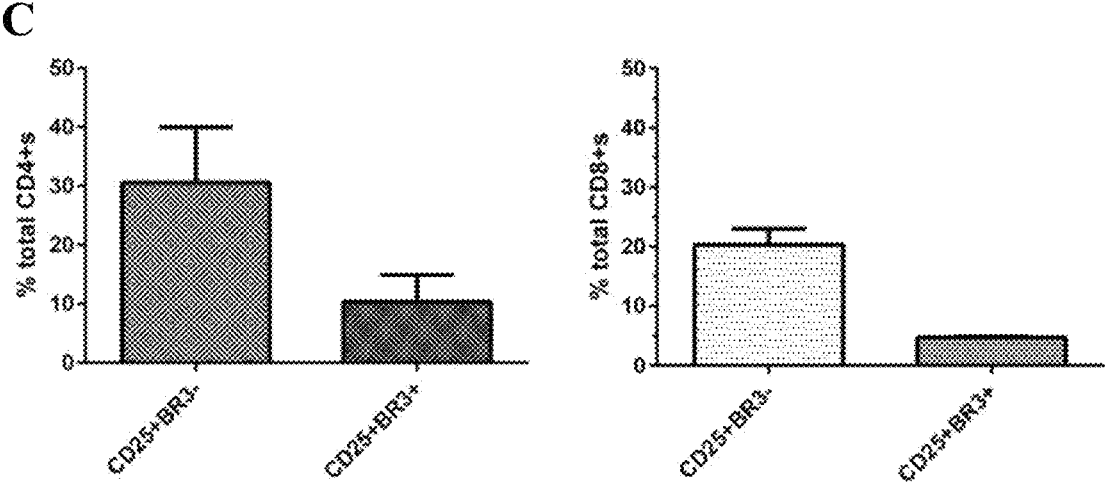
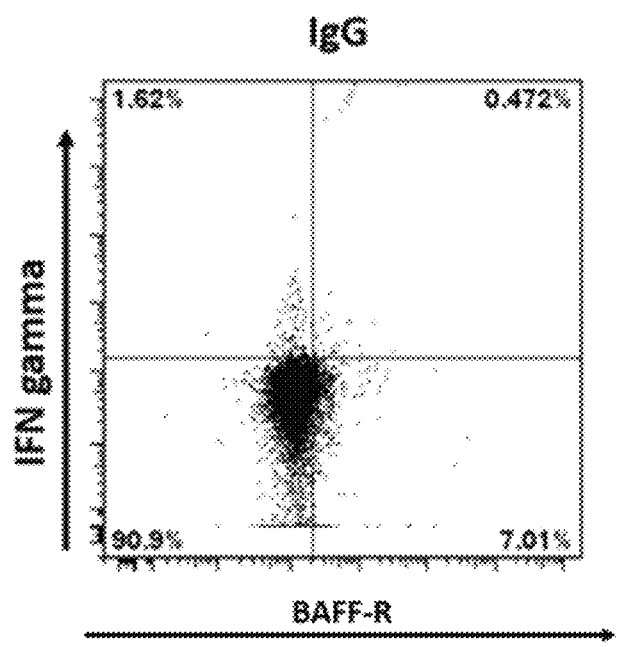

FIGS. 6A-6C
A
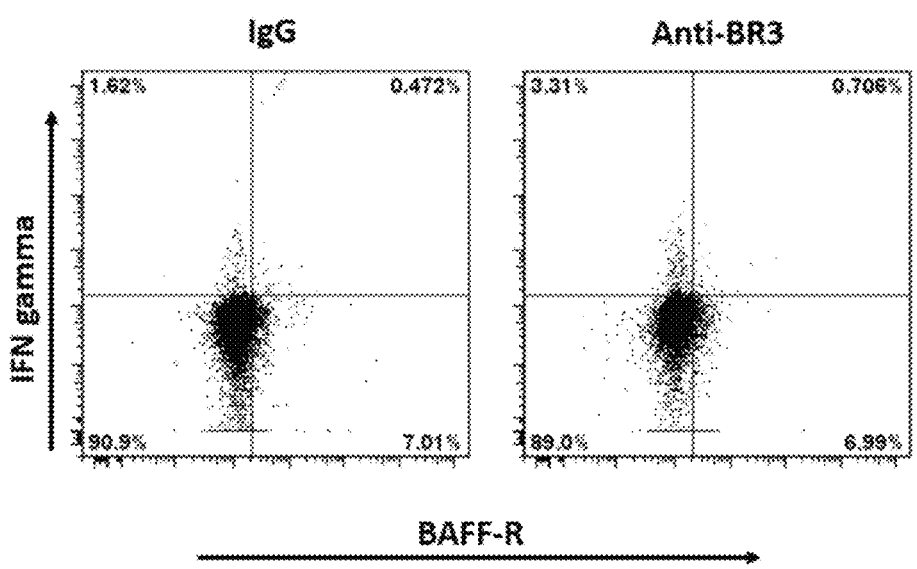
B
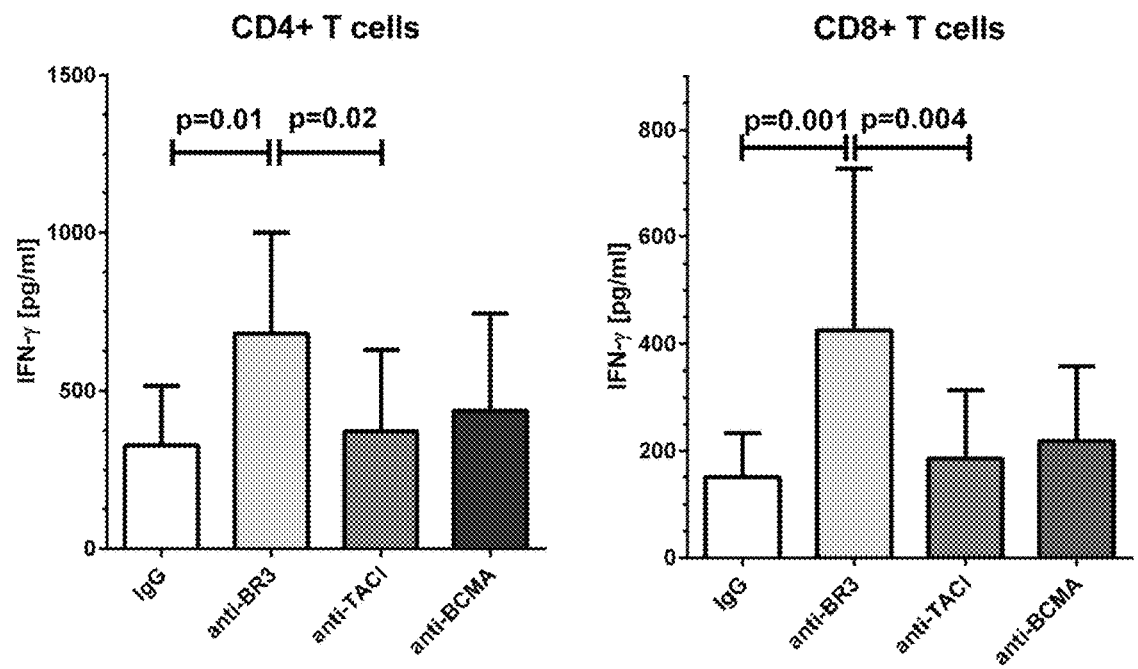

FIGS. 7A-7C
A
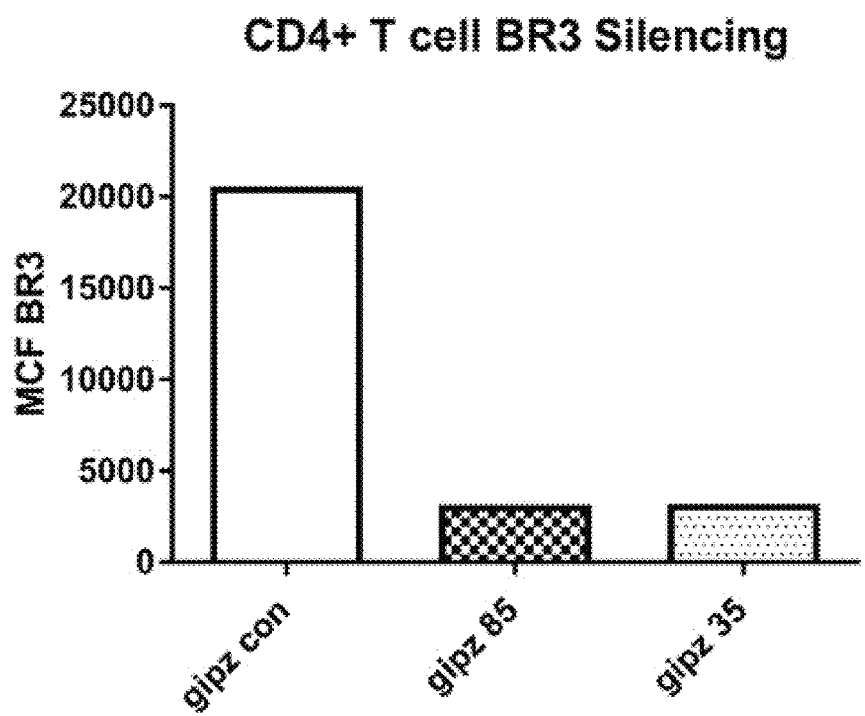
B
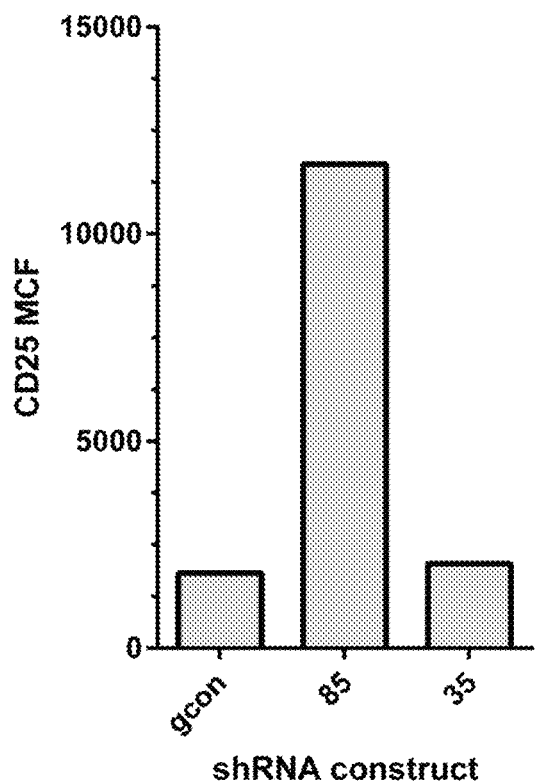

C

METHODS OF T CELL EXPANSION AND ACTIVATION

CROSS-REFERENCE TO RELATED APPLICATIONS

This application claims priority to U.S. Provisional Patent Application No. 62/307,989, filed Mar. 14, 2016, which is incorporated by reference as if fully set forth in its entirety.

STATEMENT REGARDING FEDERALLY FUNDED RESEARCH

This invention was made with government support under HHSN268201000010C awarded by the National Institutes of Health. The government has certain rights in the invention.

BACKGROUND

T-cell based immunotherapy is a rapidly growing field that has experienced impressive clinical anti-cancer successes in the last few years. In particular, it is now possible to generate human T cells that display desired specificities and enhanced functionalities compared with the natural immune system. Ex vivo expansion and activation of T cells are pre-requisites for any form of T cell immunotherapy. Several expansion and activation methodologies have been developed including (i) use of IL-2 to expand Tumor Infiltrating lymphocytes (TILs) isolated from solid tumors, (ii) use of antigen presenting cells, and (iii) use of anti-CD3 and anti-CD28 to activate chimeric antigen receptor (CAR) T cells. However, widespread utilization of T cell immunotherapies for treatment of malignancies and infectious diseases has been hindered by the lack of rapid, cost-effective, and efficient methods for selecting and expanding clinical-grade, therapeutic T cell products that proliferate and persist in vivo. Accordingly, there remains a need in the art for more robust methodologies for expanding T cell populations having clinical therapeutic potential.

SUMMARY OF THE DISCLOSURE

In one aspect, provided herein is a method of preparing a population of T cells, the method comprising reducing BAFF-R receptor activity in the T cells and culturing the T cells for about 3 to about 14 days in the presence of an anti-CD3 antibody, or a CD3-binding fragment thereof, and an anti-CD28 antibody, or a CD28-binding fragment thereof, under conditions appropriate for activating cytotoxic T cells, wherein the reducing and culturing activates and induces proliferation of activated T cells to yield a population comprising activated T cells in sufficient numbers for use in therapy.

In one embodiment, the T cells are selected from the group consisting of a leukocyte-containing cell mixture and a purified T cell population. In one embodiment, the leukocyte-containing cell mixture or purified T cell population is obtained from apheresis of peripheral blood of a human subject. In another embodiment, the leukocyte-containing cell mixture or purified T cell population is obtained from peripheral blood mononuclear cells of a human subject.

In one embodiment, the population of activated T cells comprises at least one of activated $CD4^+$ T cells and $CD8^+$ T cells. In another embodiment, cytotoxic $CD8^+$ T cells are preferentially expanded from the activated T cell population.

In some embodiments, the method of reducing BAFF-R receptor activity in the T cells is selected from the group consisting of culturing T cells in the presence of a BAFF-R antagonist and contacting T cells with a BAFF-R specific shRNA. In one embodiment, the BAFF-R antagonist is a neutralizing BAFF-R antibody.

In another aspect, provided herein is a method of preparing a population of T cells, the method comprising reducing BAFF-R receptor activity in the T cells, culturing the T cells for about 3 to about 14 days in the presence of an anti-CD3 antibody, or a CD3-binding fragment thereof, and an anti-CD28 antibody, or a CD28-binding fragment thereof, under conditions appropriate for activating cytotoxic T cells, and providing in the T cells a chimeric antigen receptor, to generate a population of activated T cells comprising the chimeric antigen receptor.

In some embodiments of the present invention, the step of providing in the T cells a chimeric antigen receptor is selected from the group consisting of introducing the chimeric antigen receptor into the T cells and transfecting a nucleic acid vector encoding the chimeric antigen receptor into the T cells whereby the T cells express the chimeric antigen receptor.

In another aspect, provided herein is an ex vivo cultured T cell population comprising human T cells prepared according to the methods described herein.

In another aspect, provided herein is a method of treating a disease in a subject in need thereof, the method comprising administering to the subject a therapeutically effective amount of the T cell population produced by the methods described herein, wherein administering treats the disease in the subject, wherein the disease is selected from the group consisting of cancer and infection.

In some embodiments, the cancer is a blood malignancy. In some embodiments, the blood malignancy is leukemia or lymphoma. In some embodiments, the infection is selected from the group consisting of bacterial, viral, fungal, and parasitic. In some embodiments, the T cells are administered in a pharmaceutical composition. In one embodiment, the T cells are administered by intravenous injection.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

FIGS. 2A and 2B depict data from two different donor PBL samples.

FIGS. 3A-3C demonstrate the effects of BAFF Receptor blockade on CD8+ T cell activation and proliferation. Antibodies which block ligand binding to BAFF receptors BR3, TACI, and BCMA were added to PBL cultures in which T cells were activated with anti-CD3c and anti-CD28. Blocking antibodies were added at Day 0 and T cell proliferation was analyzed on Day 4 by flow cytometry using an anti-CD8 APC antibody. Goat IgG is the control antibody for anti-BR3 and anti-BCMA. Mouse IgG1 is the control antibody for anti-TACI. (A) Proliferation of CD8+ T cells in the presence of BAFF receptor blockade. (B) ELISA analysis of IFN-γ levels in the supernatants of PBL cultures. Shown are the differential levels of two different PBL donors. (C) ELISA analysis of granzyme B levels in the supernatants of the PBL (activated T cell) cultures. Experiments were performed using two different PBL donors.

FIGS. 4A-4D show flow analysis of BR3 on CD4 and CD8 T cells in relation to markers of activation. (A) BR3 percentages on resting and activated human T cells using anti-BR3 antibody clone 11C1. T cell subsets were purified and stimulated with plate-bound anti-CD3 and anti-CD28 for 21 hours after which they were stained for anti-BR3-PE for flow cytometric analysis. (B) Resting and stimulated dot plots of CD25 and BR3. (C) BR3+ vs. BR3-CD25 expression on activated T cells. (D) BR3 vs. IFN-gamma dot plot. IFN-gamma was detected using intracellular flow cytometry. T cells were stimulated as above for 18 hours and incubated with Brefeldin A for 6 hours. Cells were then fixed, permeabilized, and stained with anti-BR3 PE and anti-IFN-gamma APC.

FIG. 9A depicts granzyme B expression, as measured by PCR and ELISA assay, in anti-CD3/CD28 activated CD4+ and CD8+ T cells with anti-BR3 or the goat IgG control. Granzyme B augmentation is specific for BR3 neutralization and is not increased with TACI or BCMA neutralization. Perforin is not increased with anti-BR3. (B) CRTAM is expressed on cytolytic CD4+ and activated CD8+ cells. Anti-BR3, but not anti-TACI and anti-BCMA neutralizing antibodies, increase CD25 expression on CRTAM+ cells as measured by flow cytometry. The increase in the median channel fluorescence of CD25 is greater on CRTAM+CD4+ T cells than for CRTAM+CD8+ T cells. (C) Anti-BR3 blockade increases killing of myeloma cell line U266 by CD4+ T cells. Killing was measured by the release of LDH using a cytotoxicity kit (Bio-Rad, Inc.) (D) Anti-BR3 increases T cell killing of melanoma cell line A375. Shown is the depletion of adherent A375 cells after a 3 day co-culture with T cells stimulated with anti-CD3/CD28, with the goat IgG control or anti-BR3.

DETAILED DESCRIPTION

Figure 1A:
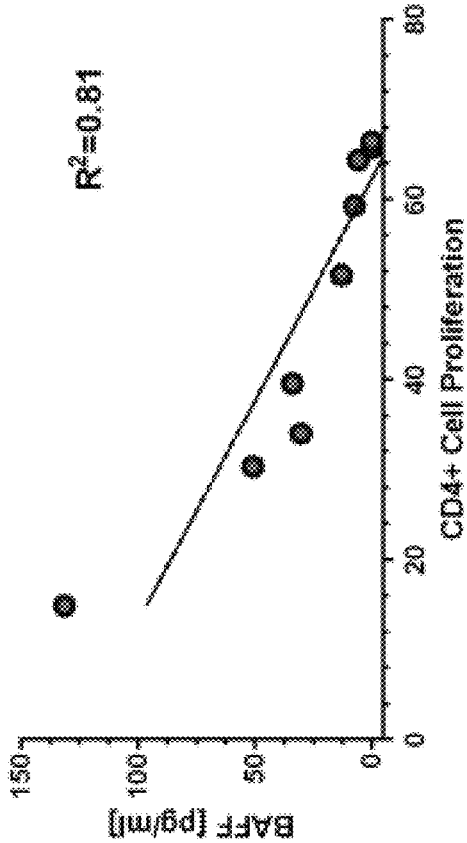
FIGS. 1A-1B demonstrate down modulation of MSC-BAFF via siRNA gene silencing. (A) Correlation of BAFF levels and T cell proliferation. Shown is a representative graph for a single MSC line that was transfected with seven different BAFF siRNA constructs. BAFF levels correlated inversely with T cell proliferation. Correlation coefficients ranged from 0.72-0.81. (B) MSCs also express IL-6. As a control, IL-6 levels were analyzed in each of the supernatants and correlated to T cell proliferation. IL-6 expression failed to correlate with degree of T cell proliferation.

The methods disclosed herein are based at least in part on the inventors' discovery of the role of BAFF (B cell activating factor) and APRIL (a proliferation-induced ligand) in T-cell suppression. BAFF is a key regulator for B cell differentiation and is critical in regulating survival and activation of peripheral B cell populations. BAFF binds to three TNF receptor superfamily members: B cell maturation antigen (BCMA/TNFRSF17), transmembrane activator and calcium-modulator and cyclophilin ligand interactor (TACI/TNFRSF13B), and BAFF receptor (also known as BAFF-R/BR3/TNFRSF13C/BLyS receptor 3 and TNFRSF13C). These receptors are type III transmembrane proteins that lack a signal peptide. Whereas TACI and BCMA bind both BAFF and another TNF superfamily ligand, APRIL (a proliferation-inducing ligand), BAFF-R selectively binds BAFF.

As described for the first time herein, the addition of either MSC-derived BAFF/APRIL or recombinant BAFF/APRIL to interferon gamma-activated MSC cultures can increase the expression and activity of the enzyme indoleamine 2,3-dioxygenase (IDO1), which catalyzes degradation of the essential amino acid L-tryptophan to N-formylkynurenine. BAFF and APRIL seem to act as a toggle switch for IDO1 expression. Without being bound by any particular theory, it is believed that down-regulating IDO1 by specifically blocking the BAFF/APRIL receptor that augments expression will decrease leukocyte functions and increase proliferation of effector T cells.

Accordingly, the present disclosure relates to methods, cells, and compositions for preparing cell populations and compositions for adoptive cell therapy. In particular, provided herein are efficient and effective methods for robust expansion and activation of T cell populations for genetic engineering and adoptive T cell immunotherapies. Methods of the present invention provide for the preparation of T cells for use in therapeutic methods by selectively activating particular T cell populations. Also provided are cells and compositions produced by the methods and methods of their use. The present disclosure also relates to methods for the stimulation of T cell activation and expansion in vivo and in vivo administration of anti-BAFF-R agents.

Methods

In a first aspect, provided herein are robust methods of preparing a population of T cell by expanding and activating T cells ex vivo. As used herein, the term "ex vivo" refers to a condition that takes place outside an organism. In the context of this disclosure, treatment of immune cells ex vivo means exposing such cells to certain biological molecules (e.g., agonists, antagonists) in vitro (i.e., outside of an organism), preferably under sterile conditions. In some cases, ex vivo methods additionally include culturing immune cells that have been isolated from a human prior to administration back into the same human subject.

In a first step, the BAFF receptor is down regulated or blocked in a population of T cells such that the activity of the BAFF receptor is eliminated or reduced. The BAFF receptor may be down regulated or blocked by any suitable method or technique known in the art. Known methods for down regulation of gene expression or decreasing the activity of a receptor include, but are not limited to, CRISPR, microRNA, shRNA, RNAi, neutralizing antibodies, small molecule inhibitors, chemical inhibitors blocking downstream signaling pathways, and the like. In some embodiments, BAFF receptor activity or gene expression is reduced by between 1%-100% (i.e., 1%, 5%, 10%, 15%, 20%, 25%, 30%, 35%, 40%, 45%, 50%, 55%, 60%, 65%, 70%, 75%, 80%, 85%, 90%, 95%, 98%, 99%, 100%). In one embodiment, T cells are cultured in the presence of a BAFF Receptor antagonist. In one embodiment, T cells are contacted with a BAFF-R specific shRNA to reduce BAFF-R gene expression.

In one embodiment, T cells are cultured in the presence of a BAFF Receptor antagonist. In exemplary embodiments, the BAFF receptor antagonist is a neutralizing antibody that reacts with the B cell activating factor receptor (BAFF-R). Human anti-BAFF-R antibodies are available from commercial suppliers such as R&D Systems and Invitrogen.

Preferably, the T cells are in a leukocyte-containing cell mixture or purified T cell population. In some cases, leukocyte-containing cell mixtures or purified T cell populations are obtained from, for example, apheresis of peripheral blood of a human subject or peripheral blood mononuclear cells of a human subject. As used herein, the term "leukocyte-containing cell mixture" refers to a cell population or cell composition comprising leukocyte cell type including granulocytes, lymphocytes and monocytes. A leukocyte-containing cell mixture preferably comprises one or more specific leukocyte cell types. A preferred cell type is the lymphocyte, especially a T-lymphocyte ("T cell"). As used herein, the term "purified T cell population" refers to T cells isolated, separated, or otherwise removed from the blood or a leukocyte milieu (e.g., obtained by leukapheresis), whereby isolated/separated T cells exist in a physical milieu distinct from that in which they occur in vivo. The term does not imply any particular degree of purity, and the absolute level of purity is not critical. Those skilled in the art can readily determine appropriate levels of purity for use according to the methods provided herein.

In one embodiment, T cells are contacted with a BAFF-R specific shRNA to reduce BAFF-R gene expression. A suitable shRNA for the present invention is one that is able to direct cleavage and subsequent degradation of complementary BR3 mRNA. Suitable shRNA constructs are commercially available. For example, shRNA constructs may be purchased from Dharmacon Inc.

In a next step, T cells in which the BAFF receptor has been down regulated or blocked are cultured for about 3 to about 14 days (e.g., about 3, 4, 5, 6, 7, 8, 9, 10, 11, 12, 13, 14 days) in the presence of an anti-CD3 antibody, or a CD3-binding fragment thereof, and an anti-CD28 antibody, or a CD28-binding fragment thereof, under conditions appropriate for activating T cells. In vitro T cell expansion using this about 3 to about 14 day culture step activates and induces proliferation of such cultured T cells to yield an expanded population comprising activated cytotoxic T cells in sufficient numbers for use in therapy. The expanded T cell population can comprise CD4-positive T cells or CD8-positive T cells. In some cases, cytotoxic $CD8^+$ T cells are preferentially expanded from the activated T cell population.

Conditions appropriate for activating T cells include any medium suitable to maintain the viability of the T cells and any formulation of the anti-CD3 and anti-CD28 antibodies such that the antibodies are able to contact the T cells. In some embodiments, the anti-CD3 and anti-CD28 antibodies may be affixed to a solid substrate such as a bead or the surface of a plate. In some embodiments, the anti-CD3 and anti-CD28 antibodies are soluble. In one embodiment, an exemplary culture medium for culturing leukocytes is RPMI 1640 cell culture medium or a similar cell culture medium. Optionally, the medium may contain up to about 25% heat-inactivated human serum albumin. A BAFF-R antagonist is added to the culture medium, and incubation with the BAFF-R antagonist can be performed at any appropriate temperature (e.g., 4° C., 25° C., or 37° C.). Preferably, BAFF-R antagonist incubation occurs at 37° C. Suitable treatment duration can be conveniently optimized by one of ordinary skill in the art. Preferably, the treatment time is about 1 hour to about 24 hours. Exemplary BAFF-R antagonist amounts for contacting to leukocytes include about 0.1 μg/ml to about 100 μg/ml. One of skill in the art could easily determine the useful amounts of BAFF-R antagonist to reduce or eliminate BAFF-R activity.

T cells are broadly divided into cells expressing CD4 on their surface (also referred to as CD4-positive cells) and cells expressing CD8 on their surface (also referred to as CD8-positive cells). T cells appropriate for use according to the methods provided herein are mononuclear lymphocytes (PBLs) derived from bone marrow (BM) or peripheral blood (PB) of a human donor. These cells could be collected directly from BM or PB or after mobilization or stimulation via administration of growth factors and/or cytokines such as granulocyte-colony stimulating factor (G-CSF) or granulocyte-macrophage colony-stimulating factor (GM-CSF) to allogeneic or autologous donors. Those skilled in the art would appreciate that there are many established protocols for isolating peripheral blood mononuclear cells (PBMC) from peripheral blood. Human peripheral blood may be drawn conveniently via venipuncture. Isolation of PBMC can be aided by density-gradient separation protocols, usually employing a density-gradient centrifugation technique using Ficoll®-Hypaque or Histopaque® for separating lymphocytes from other elements in the blood. Preferably, PBMC isolation is performed under sterile conditions. Alternatively, cell elutriation methods may be employed to separate mononuclear cell populations. The advantages of the cell elutriation method include sterility and efficiency.

In exemplary embodiments, the methods provided herein include activating BAFF-R-contacted leukocytes with a stimulus that induces T-cell activation. Exemplary stimuli include, but are not limited to, mitogens such as Concanavalin A, IL-2, and anti-CD2-, anti-CD3-, or anti-CD28 beads. CD28 (also known as T90/44 antigen or Tp44) is a T-cell surface expressed antigen that is a receptor for costimulatory proteins acting on T cells. CD3 is a complex of at least five membrane bound polypeptides in mature T-lymphocytes that are non-covalently associated with one another and with the T cell receptor. The CD3 complex includes gamma, delta, epsilon, zeta, and eta subunits. When antigen binds to the T cell receptor, the CD3 complex transduces the activating signals to the cytoplasm of the T cell. For example, cross linking T cell receptors with anti-CD3 monoclonal antibody (mAb) leads to T cell activation, proliferation, cytokine synthesis, and non-specific cytotoxicity directed at tumor targets. These activated T cells are characterized by increased IL-2 production, exhibit non-MHC restricted cytotoxicity, and produce IFNγ, TNFα, and GM-CSF.

In some cases, methods of this disclosure further include introducing a genetically engineered or chimeric antigen receptor into activated T cells, wherein the method thereby generates an expanded population comprising $CD4^+$ T cells and $CD8^+$ T cells expressing the genetically engineered or chimeric antigen receptor. Chimeric antigen receptors (CARs), also known as chimeric T cell receptors, artificial T cell receptors and chimeric immunoreceptors, are engineered receptors, which graft specificity onto an immune effector cell. In general, a chimeric antigen receptor is a transmembrane protein having a target-antigen binding domain that is fused via a spacer and a transmembrane domain to a signaling endodomain. When the CAR binds its target antigen, an activating signal is transmitted to the T-cell. In one embodiment, the chimeric antigen receptor or genetically engineered receptor is introduced into the T cells. In one embodiment a nucleic acid vector encoding the chimeric antigen receptor or genetically engineered receptor is transfected into the T cells whereby the T cells express the chimeric antigen receptor.

Reagents and other materials used during ex vivo manipulation procedures, for example antibodies, cytokines, serum, other chemicals, or solid supports such as beads and especially the virus-based gene vectors, should be compatible with aseptic production of a therapeutic cell product.

Expanded T cell populations obtained according to a method provided herein are useful for cellular immunotherapies including, without limitation, T cell therapy, adoptive cell therapy (ACT), and CAR T cell therapy. As used herein, the term "adoptive cell therapy" refers to the transfer of lymphocytes to mediate an effector function. For example, expanded T-cell populations obtained as described herein can be used in an ACT method to reverse in vivo and in vitro functional T-cell defects in patients having cancer (e.g., lymphoma). Adoptive T-cell therapies include administration of T cells that have been engineered to express chimeric antigen receptors, administration of tumor-infiltrating lymphocytes without genetic modifications (TILs), and administration of T cell receptor (TCR) engineered T cells. T-cell checkpoint therapies and TIL therapies exploit the intrinsic tumor recognition capacity of the T-cell compartment. Adoptive therapy with gene-modified T cells has the potential to address an entirely different need by creating a tumor-specific T cell compartment that is otherwise absent from patients. As such, gene-modified ACT has potential for tumor types that may not be responsive to T cell checkpoint or TIL therapies, such as most cancers occurring in children and many of the hematological malignancies. In addition, T cell checkpoint therapies and gene-modified ACT have the potential to work synergistically. Accordingly, it is contemplated that adoptive cell therapy using T cells obtained according to the methods provided herein can be combined with additional therapeutic technologies such as checkpoint-blocking antibodies, vaccines, and targeted drug therapies.

Donor lymphocyte infusions (DLIs) induce direct and potent graft versus tumor (GVT) effects, which are particularly effective for patients who relapse after allogeneic stem cell transplantation (SCT) with a donor graft. It can be advantageous to use ex vivo-activated DLI (aDLI) for some leukemia patients. In such cases, activated donor T cells are produced by co-stimulation and expansion following exposure to magnetic beads coated with anti-CD3 (OKT3) and/or anti-CD28. Generally, co-stimulation of T cells via CD3 and CD28 can produce activated T cells that can overcome disease-induced anergy, preserve and augment CD4 function, and enhance GVT activity. T cells obtained according to a method provided herein can be infused into a subject (e.g., a subject having relapsed disease after allogeneic SCT).

In some cases, it can be advantageous to simultaneously isolate and activate (stimulate) T cells from a PBMC product. For example, magnetic beads coated with anti-CD3 and anti-CD28 (i.e., the CTS Dynabeads CD3/CD28) can be used in combination with a large magnet to sort magnetic bead-attached cells from those not bound to magnetic beads.

Also contemplated herein are methods for the administration of an anti-BAFF-R agent to a subject for the stimulation of T cell activation and expansion in vivo. As used herein "anti-BAFF-R agent" refers to an entity that inhibits or reduces the activity or gene expression of the BAFF-R receptor. Anti-BAFF-R agents may include, but are not limited to, inhibitory anti-BAFF-R monoclonal antibodies, small molecule inhibitors, shRNA, shRNA vectors, microRNA, microRNA vectors, and the like. It is envisioned that treatment strategies utilizing the expanded populations of T cells obtained according to a method provided herein can be supplemented or replaced with an anti-BAFF-R agent for the activation and expansion of T cells in vivo.

Expanded populations of T cells obtained according to a method provided herein are useful for treating or preventing various disorders such as a cancer (e.g., a blood malignancy such as lymphoma or leukemia or a solid tumors such as melanoma or kidney cancer) or an infectious disease such as HIV. As used herein, the terms "treat" and "treating" refer to both therapeutic and prophylactic or preventive measures, wherein the object is to prevent or slow down (lessen) an undesired physiological change or pathological disorder. For purposes of this invention, treating a cancer includes, without limitation, alleviating one or more clinical indications, decreasing tumor growth or tumor cell proliferation, reducing the severity of one or more clinical indications of a cancer condition, diminishing the extent of the condition, stabilizing the subject's disease state (i.e., not worsening), delay or slowing, halting, or reversing cancer progression, and bringing about partial or complete remission. Treating cancer also includes prolonging survival by days, weeks, months, or years as compared to prognosis if treated according to standard medical practice not incorporating T cells obtained according to a method provided herein. Subjects in need of treatment can include those already having or diagnosed with cancer, as well as those prone to, likely to develop, or suspected of having cancer (e.g., lymphoma or multiple myeloma) or an infection. In some cases, the subject may have an autoimmune disease. As used herein, the terms "prevent" and "preventing" refer to prophylactic or preventive measures intended to inhibit undesirable physiological changes or the development of a disorder or condition. In exemplary embodiments, preventing a disease or condition comprises initiating the administration of T cells obtained according to a method provided herein at a time prior to the appearance or existence of the disease or condition (or a symptom thereof) such that the disease or condition, or its symptoms, pathological features, consequences, or adverse effects do not occur.

T cells obtained according to a method provided herein can be used in an adoptive cell therapy method for the treatment of cancer including malignancies including those of the hematolymphoid system (leukemias, lymphomas, multiple myeloma). Cancers appropriate for treatment as described herein include hematological malignancies such as acute myelogenous leukemia (AML), acute lymphocytic leukemia (ALL), chronic myelogenous leukemia (CML), myeloma, non-Hodgkin and Hodgkin lymphoma (e.g., relapsed, refractory, or chemotherapy-resistant non-Hodgkin lymphoma), and myelodysplastic syndrome (MDS). The terms "cancer" and "tumor" are used interchangeably herein. Other cancer appropriate for treatment include solid tumors such as melanoma, kidney, colon, lung, brain, and liver cancers.

T cells obtained according to a method provided herein can be used in an adoptive cell therapy method for the treatment of an infection. As used herein, the term "infection" describes a diseased state in which a microorganism or other infectious agent invades healthy cells, and includes any conditions or disease states caused by bacterial, viral, fungal, or parasitic (e.g., protozoan) infectious agents. For example, the term "viral infection" describes the infiltration of healthy cells by a virus (e.g., HIV), wherein the virus uses the cell's reproductive machinery to multiply or replicate and ultimately lyse the cell resulting in cell death, release of viral particles and the infection of other cells by the newly produced progeny viruses. With respect to infections, the term "treatment" further refers to the application or administration of a therapeutic where the purpose is to cure, heal, alleviate, relieve, alter, remedy, ameliorate, improve, or affect the infection, any associated symptoms of the infection, or the predisposition toward the development of the infection.

As used herein, the terms "subject" or "patient" are used interchangeably and can encompass any vertebrate including, without limitation, humans, mammals, reptiles, amphibians, and fish. However, advantageously, the subject or patient is a mammal such as a human, or a mammal such as a domesticated mammal, e.g., dog, cat, horse, and the like, or livestock, e.g., cow, sheep, pig, and the like. In exemplary embodiments, the subject is a human. As used herein, the phrase "in need thereof" indicates the state of the subject, wherein therapeutic or preventative measures are desirable. Such a state can include, but is not limited to, subjects having a disease or condition such as cancer.

In some cases, T cells obtained according to a method provided herein can be administered as a pharmaceutical composition comprising a therapeutically effective amount of T cells as a therapeutic agent (i.e., for therapeutic applications). As used herein, the term "pharmaceutical composition" refers to a chemical or biological composition suitable for administration to a mammal. Examples of compositions appropriate for such therapeutic applications include preparations for parenteral, subcutaneous, transdermal, intradermal, intramuscular, intracoronarial, intramyocardial, intracerebral, intratumoral, intraperitoneal, intravenous (e.g., injectable), or intratracheal administration, such as sterile suspensions, emulsions, and aerosols. Intratracheal administration can involve contacting or exposing lung tissue, e.g., pulmonary alveoli, to a pharmaceutical composition comprising a therapeutically effective amount of T cells. In some cases, pharmaceutical compositions appropriate for therapeutic applications may be in admixture with one or more pharmaceutically acceptable excipients, diluents, or carriers such as sterile water, physiological saline, glucose or the like. For example, T cells described herein can be administered to a subject as a pharmaceutical composition comprising a saline solution. In exemplary embodiments, a pharmaceutical composition comprising T cells expanded according to a method provided herein is capable of inducing a desired therapeutic or prophylactic effect upon administration to a subject.

Formulations may be designed or intended for oral, rectal, nasal, topical or transmucosal (including buccal, sublingual, ocular, vaginal and rectal) and parenteral (including subcutaneous, intramuscular, intravenous, intradermal, intraperitoneal, intrathecal, intraocular and epidural) administration. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology,* eds. J. Swarbrick and J. C. Boylan, 1988-1999, Marcel Dekker, N.Y.).

The preferred route may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some cases, T cells may be optionally administered in combination with one or more active agents. Such active agents include anti-inflammatory, anti-cytokine, analgesic, antipyretic, antibiotic, and antiviral agents, as well as growth factors and agonists, antagonists, and modulators of immunoregulatory agents (e.g., BAFF, APRIL, TNF-$\alpha$, IL-2, IL-4, IL-6, IL-10, IL-12, IL-13, IL-17, IL-18, IL-21, IL-35, IFN-$\alpha$, IFN-$\gamma$, CXCL13, IP-10, VEGF, EPO, EGF, HRG, Hepatocyte Growth Factor (HGF), Hepcidin, antibodies reactive against any of the foregoing, and antibodies reactive against any of their receptors). Any suitable combination of such active agents is also contemplated. When administered in combination with one or more active agents, T cells can be administered either simultaneously or sequentially with other active agents. For example, subjects may simultaneously receive T cells and one or more of the agents described herein for a length of time or according to a dosage regimen sufficient to support recovery and to treat, alleviate, or lessen the severity of a disease or condition.

In some embodiments, T cells are administered to a subject in need thereof using an infusion, topical application, surgical transplantation, or implantation. In exemplary embodiments, administration is systemic. In such cases, T cells are provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In some cases, compositions comprising T cells of the present invention are cryopreserved prior to administration.

Therapeutically effective amounts of T cells as provided herein are administered to a subject in need thereof. As used herein, the term "therapeutically effective dose" refers to any dose sufficient to prevent advancement, or to cause regression of the disease or condition at issue, or which is capable of relieving symptoms caused by the disease or condition, such as pain or swelling. The effective dose or amount, which can be administered in one or more administrations, is the amount of human T cells sufficient to elicit a therapeutic effect in a subject to whom the cells are administered. A therapeutically effective amount can be an amount between about $50 \times 10^6$ cells and about $700 \times 10^6$ cells of an ex vivo expanded T cell culture. In some cases, an effective amount is administered as a dosage comprising at least $1 \times 10^6$ cells per kilogram (kg) of body weight of the recipient. For example, the effective amount can be administered to the subject in a dose comprising at least $1 \times 10^6$ cells/kg, at least $10 \times 10^6$ cells/kg, at least $30 \times 10^6$ cells/kg, at least $100 \times 10^6$ cells/kg, or at least $1000 \times 10^6$ cells/kg.

Effective amounts will be affected by various factors which modify the action of the cells upon administration and the subject's biological response to the cells, e.g., the patient's age, sex, and diet, the severity of inflammation, time of administration, and other clinical factors. A therapeutically effective amount of T cells obtained according to a method provided herein can be administered to a subject.

Therapeutically effective amounts for administration to a human subject can be determined in animal tests and any art acceptable methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the T cells. For example, a T cell dosage for a particular subject can be increased if the lower dose does not elicit a detectable or sufficient improvement. Conversely, the dosage can be decreased if the disease or condition is treated or eliminated.

In some cases, therapeutically effective amounts of T cells can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular condition being treated, the physical condition of the subject, the type of animal being treated, the duration of the treatment, and the nature of any concurrent therapy. Following administration of T cells to an individual subject afflicted by, prone to, or likely to develop a disease or condition as described herein, the subject is observed and assessed for a positive or negative change in clinical symptoms or features of the disease or condition. For example, for methods of treating cancer in a subject, positive or negative changes during or following treatment may be determined by any measure known to those of skill in the art including, without limitation, measuring changes in tumor size.

In any of the methods of the present invention, the donor and the recipient of the T cells can be a single individual or different individuals, for example, autologous, allogeneic or xenogeneic individuals. As used herein, the term "autologous" refers to cells or tissues obtained from an individual and transplanted back into the same individual. As used herein, the term "allogeneic" refers to cells or tissues obtained from different individuals of the same species, where the donor and recipient are not genetically identical. With regard to the present disclosure, an allogeneic cell transplant or tissue graft involves transplantation of cells or tissues where the donor and recipient are different individuals of the same species. The term "xenogeneic" means that which is derived or obtained from an organism of a different species. With regard to the present disclosure, a xenogeneic cell transplant or tissue graft involves transplantation of cells or tissues where the donor and recipient are different individuals of different species.

Administration to the subject can be by local or systemic injection or by topical application. For example, T cells can be administered by intravenous injections such as drip infusions, intramuscular injections, intraperitoneal injections, intra-organ injections, or subcutaneous injections. In some cases, the subject is observed or assessed with regard to tissue maintenance, tissue repair or function, or overall condition.

Articles of Manufacture

In another aspect, the present invention provides articles of manufacture useful for adoptive cell therapy. In some cases, a kit of the present invention comprises one or more vessels containing human T cells. In particular embodiments, cells expanded and activated according to a method provided herein are provided in a kit, and in some cases the cells can be the sole component of the kit. The kit may additionally comprise reagents and materials useful for expanding and activating T cells as provided herein to obtain the desired cell product. For example, a kit can include one or more BAFF-R antagonists.

Optionally, a kit can further include one or more reagents or other components necessary for administering the T cells to a human subject in need thereof according to a method of the invention. It may be appropriate in some cases to provide T cells as a frozen aliquot in a pharmaceutically acceptable cryopreservant.

In some cases, the kit, in addition to T cells as provided herein, also includes a second therapeutic, such as a chemotherapeutic, a hormone therapeutic, and/or an immunotherapeutic, for example. The kit may be tailored to a particular cancer for an individual and comprise respective second therapeutics for that individual. In some cases, a kit further comprises one or more active agents such as, for example, anti-inflammatory, anti-cytokine, analgesic, antipyretic, antibiotic, and antiviral agents, as well as growth factors and agonists, antagonists, and modulators of immunoregulatory agents (e.g., TNF-α, interleukin-2 (IL-2), IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). Classes of pharmaceutical agents useful for treating cancer include, without limitation, glucocorticoids (e.g., prednisone), immunosuppressants (e.g., cyclosporine, methotrexate, tacrolimus, pimecrolimus, sirolimus, mycophenolate, mofetil, visilizumab, anti-thymocyte globulin (ATG)), antineoplastics (e.g., pentostatin), and antirheumatics (e.g., hydroxychloroquine, infliximab, entanercept). Also contemplated are kits comprising suitable combinations of such active agents. Provided with such vessels are instructions for human administration and a notice in the form prescribed by a governmental agency regulating the manufacture, use, or sale of biological products, which notice reflects approval by the agency of manufacture, use, or sale for human administration.

The present invention will be more fully understood upon consideration of the following non-limiting Examples. All texts, papers, and patents disclosed herein are hereby incorporated by reference as if set forth in their entirety.

EXAMPLES

Reference is now made to the following examples, which together with the above descriptions illustrate the invention in a non-limiting fashion.

Example 1—BAFF Interferes with MSC-Mediated T cell Suppression In Vitro

We have been investigating mesenchymal stem cells (MSCs) derived from the bone marrow of healthy donors to determine whether MSC-derived BAFF interferes with MSC-mediated T cell suppression in vitro. We have designed an 'immunopotency assay' (Bloom et al., 2015. *Cytotherapy* 17:140-151) whereby peripheral blood leukocytes (PBLs) obtained from healthy donors and labeled with carboxyfluorescein succinimidyl ester (CFSE) were co-cultured with titrated numbers of MSCs. T cells within the PBL milieu were stimulated with soluble anti-CD3/anti-CD28. Proliferation of T cell subsets was measured by flow cytometry. MSC-mediated inhibition was gauged against a positive control of activated T cells without MSCs. TACI-Fc (Atacicept) is a soluble TACI receptor that effectively binds BAFF and APRIL. When added to PBL:MSC co-cultures, TACI-Fc reversed CD4$^+$ T cell inhibition. The effect of down-modulating MSC-BAFF on T cell inhibition was measured.

Figure 1B:
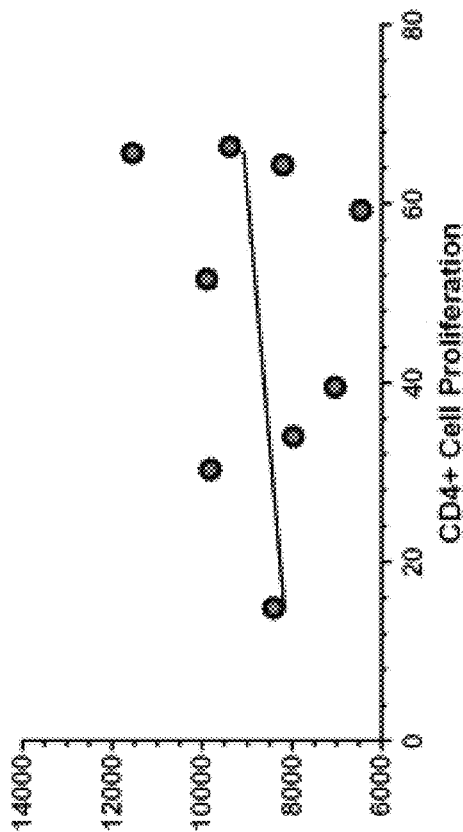

Seven different BAFF-specific shRNA plasmids were used in each of five experiments (using five different MSC lines) with subsequent PBL co-culture. Remarkably, silencing MSC-BAFF reversed T cell suppression. BAFF levels correlated inversely with CD4$^-$ T cell proliferation ($R^2$=0.81, FIG. 1A). However, IL-6 expression by MSCs was not affected by BAFF down-modulation (FIG. 1B), nor was MSC viability. Decreases in IDO1 (Indoleamine-pyrrole 2,3-dioxygenase 1) mRNA levels and enzyme activity correlated with down-modulated BAFF levels, suggesting that BAFF regulated the expression of this T cell suppression factor.

Next, BR3 function was blocked using a BR3 neutralizing antibody (R&D Systems, Inc.). In 4-day co-culture assays, we found that anti-BR3 augmented CD4$^+$ proliferation in MSC co-culture, but also enhanced CD4$^+$ proliferation in T cell-activated PBLs without MSCs, to varying degrees, depending on the PBL donor. These data suggested that BR3 was controlling the normal homeostatic suppression of at least a subset of CD4$^+$ cells.

Upon investigation of CD8$^+$ cells, a consistent increase in proliferation was observed with anti-BR3, but not observed with anti-BCMA or anti-TACI blockade (FIG. 3A). Additionally, expression of IFN-γ and granzyme B increased 9-40 fold and 3-7 fold, respectively, with BR3 blockade (FIGS. 3B-3C). Importantly, the increase in IFN-γ and granzyme B expression was not due to the anti-BR3 blocking antibody mediating indiscriminate T cell stimulation. To the contrary, human cytokine multiplex analysis demonstrated lowered or unchanged levels of other T cell cytokines. Preliminary assessments show that the IDO activity/kynurenine levels in the supernatants are decreased in anti-BR3 treated (24 hour) cultures. Importantly, anti-TACI had the opposite effect: T cell proliferation and IFN-γ expression were significantly decreased, which may explain the dual nature of BAFFs effects on T cells.

Together, these data strongly indicate that BAFF augments the expression of IDO1 and that BR3 is a primary negative regulator of cytotoxic (CD4$^+$ and CD8$^+$) T cell proliferation, IFN-γ expression, and granzyme B production. We hypothesize that one of the mechanisms of BR3-mediated suppression of cytotoxic T cell activation is its ability to enhance IDO1 expression. Our in vitro data supports the hypothesis that BAFF mediates the expression of immune suppression factors. When peripheral blood lymphocytes are stimulated with T cell stimulatory antibodies anti-CD3 and anti-CD28, proliferation of both CD4$^+$ and CD8$^+$ T cells is increased. Upon addition of antibodies which specifically neutralize the BAFF receptor BR3, both CD4$^+$ and CD8$^+$ T cell proliferation increased significantly. Interestingly, the data also revealed that blocking BR3 enhances IFN-γ production as well as the production and/or secretion of the CD8$^+$ T cell toxin granzyme B. These data strongly suggest that BR3 is one of the essential suppressors of CD8$^+$ cytotoxic T cell activation and proliferation.

Methods & Materials

Preparing Peripheral Blood Leukocytes: PBLs were isolated from blood taken from healthy individuals. Apheresis products or whole blood can be used. Cells were applied to a Ficoll-Paque gradient to purify the white blood cells away from the red blood cells and platelet contamination as previously described (Corkum et al., 2015. *BMC Immunol.* August 26; 16:48). The PBLs were viably frozen in vials with DMSO and cryopreserved in liquid nitrogen.

Antibodies and Reagents: Anti-CD3ε is a monoclonal antibody that stimulates the epsilon chain of the TCR complex on human T cells. Clone UCHT1 was purchased from R&D Systems, Inc. (cat #MAB100). The lyophilized product was resuspended in PBS at 500 µg/ml, aliquoted, and stored long term at −20° C.

Anti-CD28 is a monoclonal antibody that co-stimulates human T cells in conjunction with anti-CD3ε. Clone 37407 was purchased from R&D Systems, Inc. (cat #MAB342). The lyophilized product was resuspended in PBS at 500 µg/ml, aliquoted, and stored long-term at −20° C.

Anti-BAFF-R blocking antibody blocks human BR3. It is a goat polyclonal antibody purchased from R&D Systems, Inc. (cat #AF1162). The lyophilized product was resuspended in PBS at 200 µg/ml, aliquoted, and stored long-term at −20°.

Goat IgG control was purchased from R&D Systems, Inc. (cat #AB-108-C). The lyophilized product was resuspended in PBS at 200 µg/ml, aliquoted, and stored long-term at −20° C.

Complete RPMI Medium: RPMI-1640 with 10% FBS (heat inactivated at 55° for 30', Atlanta Biologicals), Glutamine, Non-Essential Amino Acids, HEPES, and NaPyruvate. Pen/Strep is not typically used but its addition does not alter results. Medium was filter sterilized before use.

CFSE (carboxylfluorescein diaacetate succinimidyl ester): stock concentration of 1 mM in DMSO. The fluorochrome was purchased from Invitrogen.

Anti-huCD4 APC and anti-huCD8 APC-labeled antibodies for flow cytometry were purchased from R&D Systems, Inc.

Example 2—BR3 Blockade Protocol

The study described in Example 2 demonstrates methods used for achieving a BR3 blockage in non-purified T cells for use in proliferation assays. We rapidly thawed vials containing peripheral blood leukocytes (PBLs) in a 37° C. water bath (~2 minutes) and sterilely transfer PBLs to a 15 ml conical tube and resuspend in a complete Roswell Park Memorial Institute (RPMI) culture medium. Tubes were centrifuged for 10 minutes at 1200 rpm.

The supernatant was aspirated from the cell pellet. 10 ml of D-PBS without $Ca^{2+}$ or $Mg^{2+}$ was added to the cell pellet to wash the cells. The cells were centrifuged for 10 minutes at 1200 rpm. Supernatant was aspirated from the cell pellet and no more than 1 ml PBS was added per $10 \times 10^6$ cells. 2 ul of 1 mM CFSE per 1 ml of cells was added, mixed and incubated in the dark at 37° C. for 10 minutes. An equal volume of cold (4° C.) FBS was added to stop the CFSE labeling. Cells were washed and prepared such that 200 µl of cell suspension corresponding to approximately $4 \times 10^5$ cells was added per well in a 48-well plate.

Anti-BR3 antibody or control goat anti-IgG antibody was added to each well of 48-well plate. Cells and antibodies were incubated for 30 minutes at 37° C. in an incubator containing 5% $CO_2$.

After incubation with the anti-BR3 or IgG control antibody, anti-CD3/CD28 stimulatory antibodies (preferably at a ratio of 5:1) were added to the cell culture the culture was incubated for 3-4 days for T cell expansion to proceed. To analyze proliferation, cells were harvested from each well and placed in centrifuge tubes to separate supernatants and collect cell pellets. The supernatants were stored separately at −20° for further analysis.

Samples introduced to either anti-CD4 APC or anti-CD8 APC flow antibodies and were analyzed on a flow cytometer using FL1 (CF SE) and FL4 (APC) channels. Cells were analyzed for total proliferation against a non-stimulated control (i.e., the total percentage of cells that have undergone cell division). Cell proliferation was analyzed using standard flow cytometry data analysis and modeling software, either FlowJo™ or ModFit LT™.

Example 3—Ex Vivo Co-Stimulation and Expansion of T Cells for Donor Leukocyte Infusions (DLI)

An aliquot of cells from a donor leukocyte product collected on the first or second day of leukapheresis is removed prior to DLI for ex vivo expansion. The washed apheresis product is enriched for lymphocytes using magnetic bead depletion of monocytes in a closed system if monocytes constitute more than 20% of white blood cells (WBCs) as gated on a Coulter Multisizer3 (Beckman Coulter, Fullerton, Calif.). T cells are processed in a manner consistent with appropriate FDA guidelines and regulations on Good Manufacturing Practices.

The cells are seeded into gas-permeable flasks containing X VIVO 15 (Cambrex, Walkersville, Md.) supplemented with 5% normal human AB serum (Valley Biomedical, Winchester, Va.), 2 mM L-glutamine (Cambrex), and 20 mM HEPES (Cambrex). Magnetic beads (Dynal, Brown Deer, Wis.) with conjugated anti-CD3 (OKT3; Ortho Biotech, Bridgewater, N.J.) and anti-CD28 (clone 9.3) monoclonal antibodies are added at a 3:1 bead/$CD3^+$ cell ratio, and the cultures are maintained for up to 12 days prior to harvest and preparation for infusion. After completion of cell culture, the magnetic beads are removed using a magnetic cell separation system, and the cells are washed, concentrated, and resuspended in 100 to 250 mL PlasmaLyte A (Baxter Oncology)/5% dextrose 0.45% NaCl containing 1% human serum albumin (Baxter Oncology). All infused T-cell products are required to meet release criteria specified for T-cell phenotype, cell viability, pyrogenicity, sterility, and freedom from bead contamination.

Example 4—Blockade of BAFF-R on T Cells Enhances their Activation and Cytotoxicity Materials and Methods Cell Culture and Purification: Primary human T cells were obtained from leukopheresis products purchased from AllCells, LLC (Alameda, Calif.) or Key Biologics, LLC (Memphis, Tenn.). Upon arrival, PBLs were isolated via ficoll separation and viably frozen for future use. For T cell studies, thawed PBLs were used directly in activation assays or T cell subsets purified by magnetic bead sorting. For purification, CD4 or CD8 beads from Miltenyi Biotec, Inc. (San Diego, Calif.) were used according to manufacturer protocol. An AutoMacs sorter (Miltenyi Biotec) was used for bead sorting. CD4 and CD8 T cell populations were typically 90-95% pure. All T cell assays were performed in RPMI containing 10% FBS, glutamine, HEPES, Na-Pyruvate, NEAA, and Pen/Strep. Myeloma line U266 was cultured in RPMI containing 10% FBS, glutamine, HEPES, Na-Pyruvate, NEAA, and Pen/Strep. The adherent melanoma line A375 was expanded in alpha-MEM containing 10% FBS, glutamine, NEAA, and Pen/Strep. A375 cells were grown to 70-80% confluence before passaging.

Flow Cytometry: All flow cytometry experiments were run on an Accuri C6 (BD Biosciences, Inc.) with 2 lasers for 4-color analysis. Antibodies used were as follows: anti-BR3 PE, clone 11C1, BD Biosciences; anti-CD25 FITC-Violet and APC, clone 3H3, Miltenyi Biotec; anti-IFN-g APC, clone B27, BD Biosciences; anti-Granzyme B PE, clone GB11, BD Biosciences; anti-CRTAM PE, clone Cr24.1, Biolegend, Inc. Analyses were performed using CFlowPlus (BD Biosciences) or FlowJo (TreeStar, Inc.) software.

Anti-BR3 Neutralization Assays: BAFF receptor blocking antibodies anti-BR3 (cat #AF1162), anti-TACI (cat #AF174), and anti-BCMA (cat #AF193), were purchased from R&D Systems, Inc (Minneapolis, Minn.). All three are goat polyclonal antibodies. All were received as lyophilized products. All were resuspended in PBS at the recommended concentrations, aliquoted, and frozen according to manufacturer's instructions. Care was taken to use antibody products that were thawed only once. For blocking assays, CD4 and CD8 T cell subsets were bead selected and resuspended in complete RPMI (see above) at 1×10e6/ml. Cells were pre-incubated with each neutralizing antibody or normal goat IgG control (cat #AB-108-C) at 10 ug/ml for 30 minutes at 25° C. 2×10e5 cells/well were added to 96-well flat bottom tissue culture treated plates; 4×10e5/ml were added to 48-well plates. Plates were pre-coated with 1 ug/ml anti-CD3e (clone UCHT1, R&D Systems, Inc.) and 0.2 ug/ml anti-CD28 (clone 37407, R&D Systems, Inc.) at 37° C. for 8 hours with subsequent PBS washes. Again, care was taken to use anti-CD3/CD28 antibodies thawed only once. T cells were activated and incubated for 21-24 hours in a 37° C. incubator at 5% CO2. Cells were gently harvested with wide bore pipette tips and supernatants collected and stored at −20° C.

BR3 shRNA Down-Modulation: Four shRNA plasmid constructs specific for human BAFF-R were purchased from Dharmacon, Inc. including the GIPZ shRNA control plasmid. 1-2 ug of each plasmid was introduced into 2-4×10e6 CD4 or CD8 T cells using Amaxa-based nucleofection. Amaxa kits specific for human T cell transfection were purchased from Lonza, Inc. Program V24 was used for electroporation according to manufacturer's instructions after which cells were rested for 18 hours in 12-well plates containing pre-warmed complete RPMI. Cells were then gently harvested, analyzed for live/dead, and added at 1×10e6 live cells/well to 12-well plates pre-coated with anti-CD3/CD28 (1 ug/ml and 0.2 ug/ml, respectively, as above). Transfected T cells were activated for 21-24 hours. Cells were then harvested and analyzed for BR3, CD25, and IFN-g as described above.

Cytotoxicity Assay: Cytotoxicity/target killing was measured using a CSFE/propidium iodide assay as previously described in the art. Briefly, CFSE-labeled A375 melanoma cells were co-cultured with purified CD4+ and CD8+ T cells at Teff:target ratios ranging from 30:1-5:1 for 18 hours. Cells were subsequently harvested and analyzed by flow cytometry for percent PI positive in the CFSE positive gate. T cells were gated out using anti-CD2 APC.

Semi-Quantitative PCR: RNA was isolated from activated T cell subsets treated with or without anti-BR3 for 21-24 hours. Total mRNA was isolated using RNA Easy kits (Qiagen, Inc.). cDNA was generated using a Verso cDNA Synthesis kit (Thermo Fisher Scientific, Inc.). Primers used to amplify GAPDH, CD25, CD69, IFN-g, IL-2, granzyme B, granzyme A, and perforin were all Quantitect Primers from Qiagen, Inc. A SYBR Green-based PCR kit (Applied Biosystems, Inc.) was used to amplify cDNA on a StepOne-Plus thermocycler according to previously established protocols (Hope C., et al. "TPL2 kinase regulates the inflammatory milieu of the myeloma niche," Blood, 2014, 123 (21):3305-3315).

ELISA: Tissue culture supernatants were harvested after 21-24 hours from assays noted above and frozen at −20° C. Supernatants were utilized within one month's time. Human IFN-g concentrations in culture supernatants were measured using an ELISA kit (Thermo-Pierce, Inc.). Human Granzyme B was measured using ELISA kits from eBioscience, Inc, (Platinum ELISA) and R&D Systems, Inc. (DuoSet).

Results

BR3 is Expressed on Resting and anti-CD3/CD28 Activated T cells: We began our analysis by examining the degree to which resting and anti-CD3/anti-CD28 activated T cells expressed BR3 on their cell surface in our system, using the BR3 specific antibody clone 1C11 in flow cytometry. CD4+ and CD8+ T cells purified by bead selection were rested for 24 hours or activated using plate-bound stimulatory antibodies. Using a series of different healthy blood donors, we found that there was significant surface BR3 level variability in resting CD4+ BR3+ cells (10+/−8%) whereas resting CD8+BR3+ cell percentages were significantly less variable (10+/−1%) (FIG. 4A). Using anti-CD25 (anti-IL-2Rα) antibody clone 4E3 (Miltenyi Biotec, Inc.) BR3 expression was detected on a fraction of resting CD4+ CD25hi cells, but was never more than 1% of the total resting CD4+ population (data not shown). Resting CD8+ CD25hi cells were not detected. Upon 24 hours of stimulation with plate-bound anti-CD3/CD28, BR3 expression increased to an average of 25% on CD4+ T cells and 12% on CD8+ T cells.

CD25 and CD69 are established markers of T cell activation. In our system, using plate-bound stimulatory antibodies anti-CD3 at 1 ug/ml and anti-CD28 at 0.2 ug/ml, 30-50% of T cells expressed CD25 at 24 hours. Greater than 90% of CD25+ cells co-expressed CD69. However, only a minor fraction of BR3+ cells were CD25+/CD69+. On average, 30% of CD4+ BR3+ T cells co-expressed CD25 whereas only 20% of CD8+BR3+ cells expressed CD25 (representative dot plot FIG. 4B, averages FIG. 4C). This suggested that BR3 was not ubiquitously expressed on activated T cells. Importantly, the majority of CD4+BR3+ and CD8+BR3+ populations did not produce IFN-γ at 24 hours post-activation as determined by intracellular flow cytometry (FIG. 4D). 75-90% of IFN-γ+ cells were CD25+ BR3−. This suggested that BR3 was not expressed on most functionally active effector cells in our system.

Importantly, we were able to detect BAFF receptors BCMA and TACI on activated CD4+ and CD8+ lymphocytes. Flow cytometric analysis demonstrated 10-20% BCMA+ T cells and 2-5% TACI+ cells 24 hours post-stimulation (data not shown). PCR analysis verified relative BCMA and TACI protein levels (data not shown). As such, all three BAFF receptors were expressed on activated human T cells in this study.

Anti-BR3 Neutralization Increases CD25 Expression: We hypothesized that if BR3 co-stimulated human T lymphocytes, as has been suggested by other studies, then a BR3 neutralization antibody should decrease CD25 expression and reduce cytokine expression in TCR-stimulated T cells. We used the only commercially available BR3 blocking antibody for our studies, a goat polyclonal antibody from R&D Systems, Inc. A recombinant protein which spans the BAFF binding site on BR3, amino acids 71-121, was used to generate the blocking antibody. Goat IgG as well as anti-TACI and anti-BCMA goat polyclonal blocking antibodies (also from R&D Systems) served as controls. Importantly, B cells within a PBL milieu demonstrated decreased survival in the presence of the anti-BR3 antibody (data not shown) and we therefore proceeded with its application toward T cell activation.

Figures 5A, 5B, 5C:
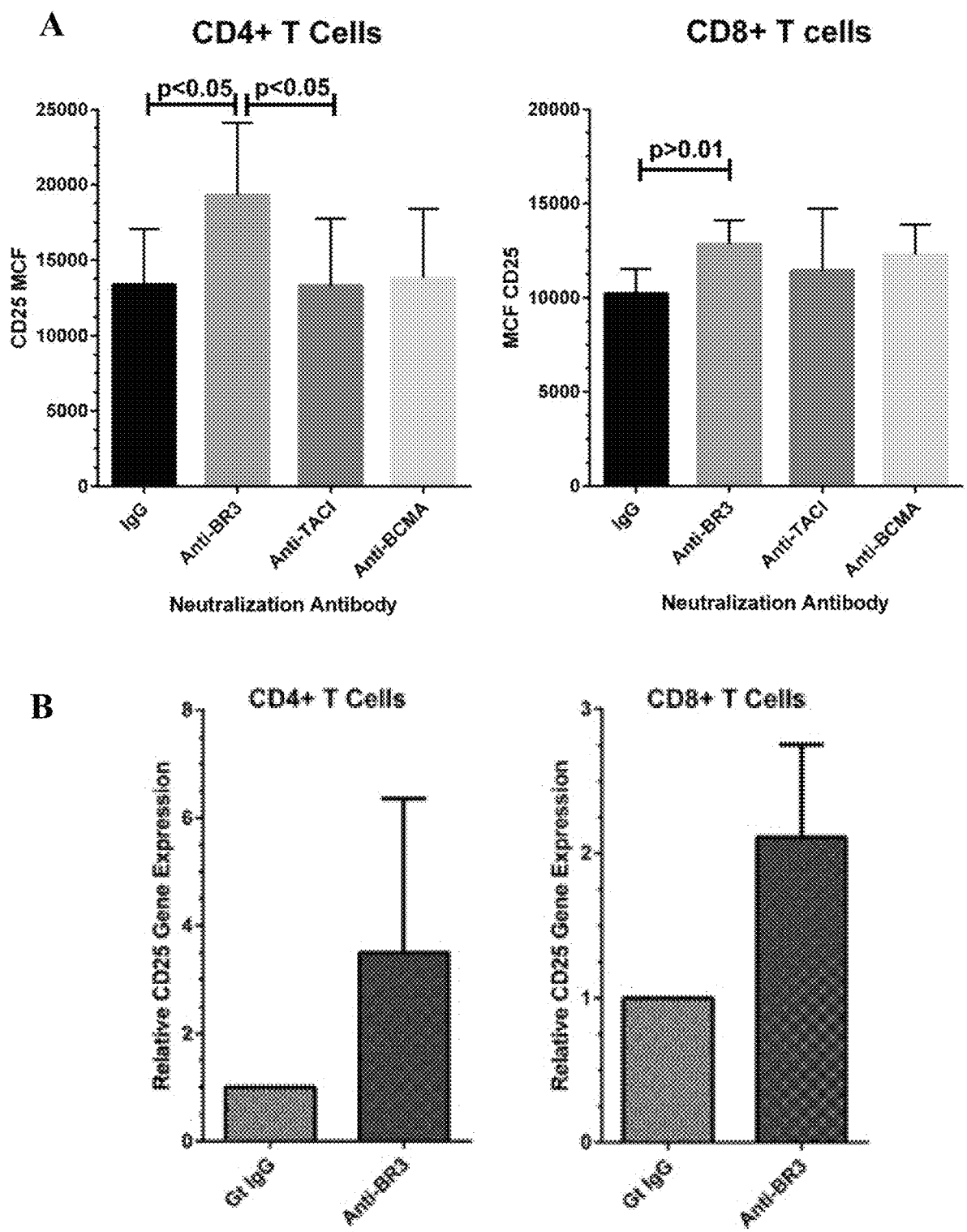
FIGS. 5A-5C demonstrates that anti-BR3 mediated blockade increases T cell activation as gauged by CD25 (IL2-R-alpha) expression. (A) Flow cytometry of increased CD25 expression in CD4+ and CD8+ T cells treated with anti-BR3 and activated for 21 hours. (B) Semi-quantitative PCR of CD25 mRNA in CD4+ and CD8+ T cells. CD25 expression was measured in relation to GAPDH expression in T cell subsets activated for 21 hours. (C) CD25 cell surface expression increases with anti-BR3 in the presence of exogenous BAFF added at nanogram/ml concentrations, levels that are found in tumor microenvironments.
Figures 5A, 5B, 5C:
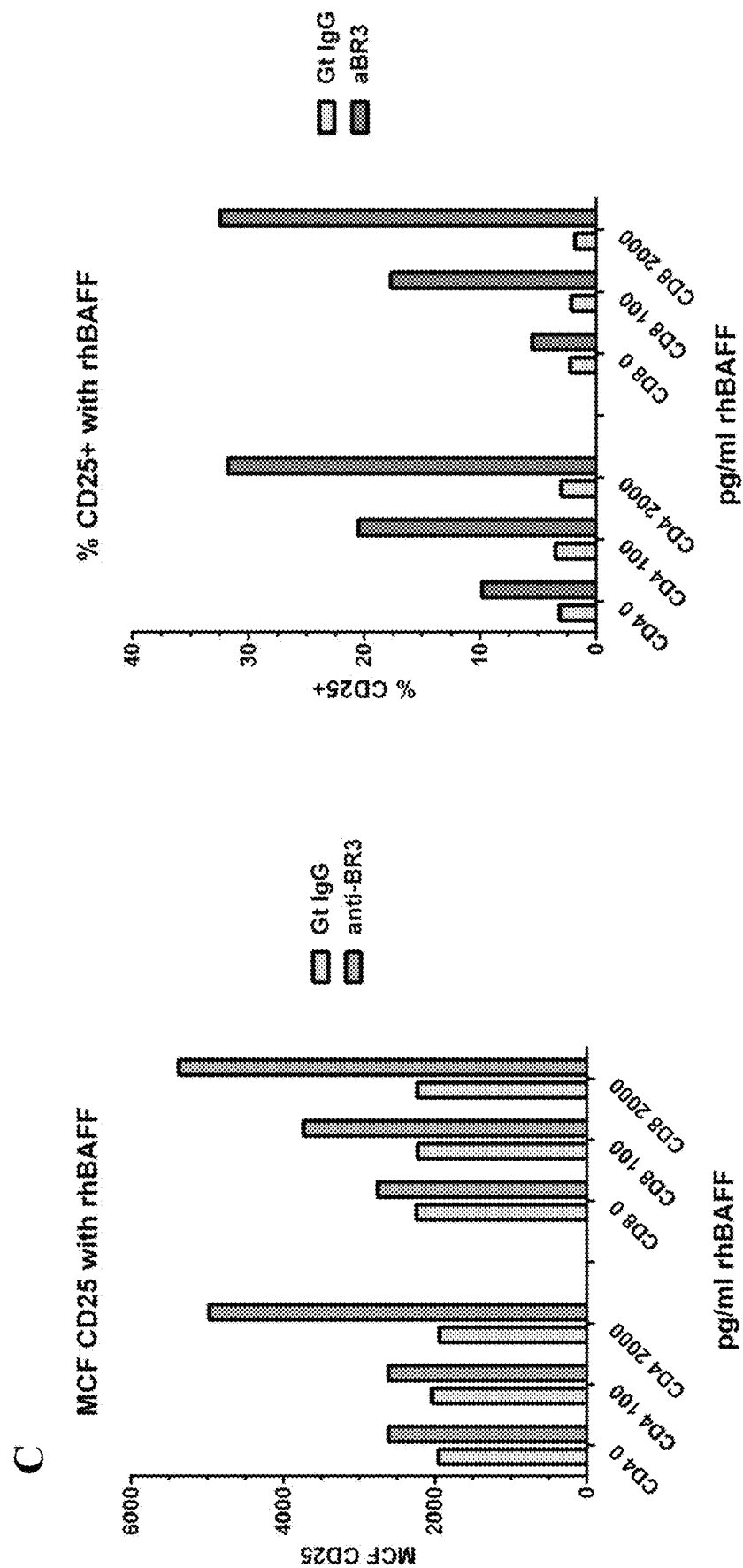

Purified CD4+ and CD8+ T cells were pre-incubated with each neutralization antibody for 30 minutes before stimulating with anti-CD3/CD28 for 21-24 hours. CD25 expression was measured by flow cytometry and semi-quantitative PCR. Flow analysis of CD25 expression revealed that anti-BR3 blockade increased the percent of CD4+CD25+CD69+ and CD8+CD25+CD69+ cells and significantly increased the Median Channel Fluorescence (MCF) of CD25 (FIG. 5A). The goat IgG control, anti-TACI, and anti-BCMA had no significant effect on CD25 expression. CD25 mRNA expression increased 2-6 fold for CD4+ cells, and 2-3 fold for CD8+ cells (FIG. 5B). The MCF of CD69 as well as CD69 mRNA expression remained unchanged with BR3 blockade (data not shown).

Figures 2A, 2B:
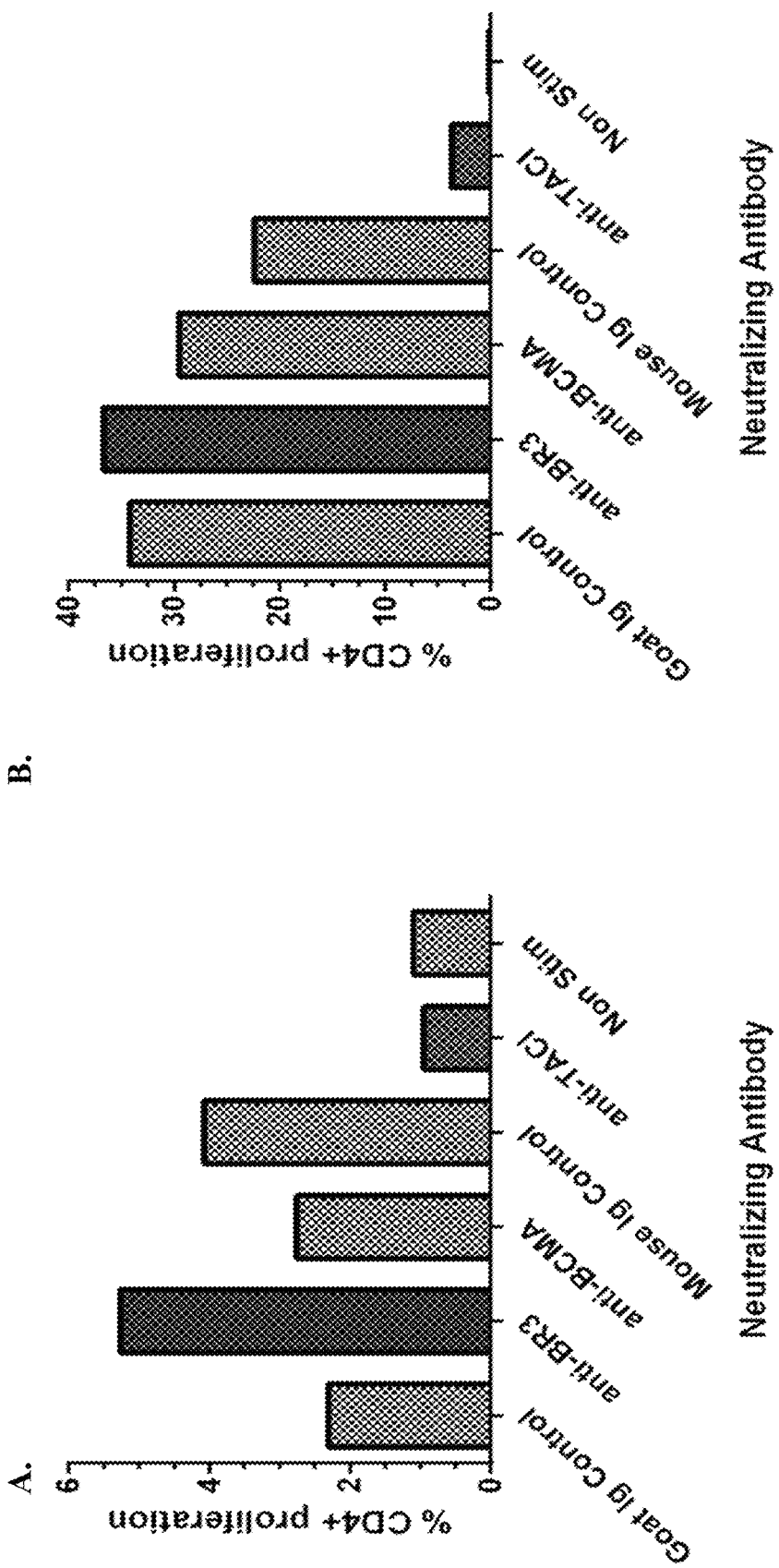
FIGS. 2A-2B demonstrate the effects of BAFF Receptor blockade on CD4+ T cell proliferation. Antibodies which block ligand (BAFF and APRIL) binding to BAFF receptors BR3, TACI, and BCMA were added to PBL cultures in which T cells were activated with anti-CD3c and anti-CD28. Blocking antibodies were added at Day 0 and T cell proliferation was analyzed on Day 4 by flow cytometry using an anti-CD4 antigen-presenting cell (APC) antibody. Goat IgG is the control antibody for anti-BR3 and anti-BCMA. Mouse IgG1 is the control antibody for anti-TACI.

These data suggested that BR3 may be suppressing T cell activation. However, we were blocking the binding of endogenous BAFF expressed on and released by activated T cells over 24 hours. Therefore, soluble BAFF levels were relatively low, ranging between 10-30 pg/ml in culture supernatants (data not shown). We wondered if CD25 expression would decrease with BR3 blockade in the presence of high concentrations (2 ng/ml) of soluble recombinant human BAFF, levels typically detected in autoimmune disease and tumor microenvironments. T cells were pre-treated with the anti-BR3 blocking antibody and then stimulated with anti-CD3/CD28 in the presence of 0.1-2 ng/ml rhBAFF for 24 hours. As shown in FIG. 2C, CD25 expression was significantly increased with BR3 neutralization by both CD4+ and CD8+ cells. These experiments suggest that BR3 suppresses T cell activation even in the presence of high soluble BAFF concentrations.

Figures 6A, 6B, 6C:
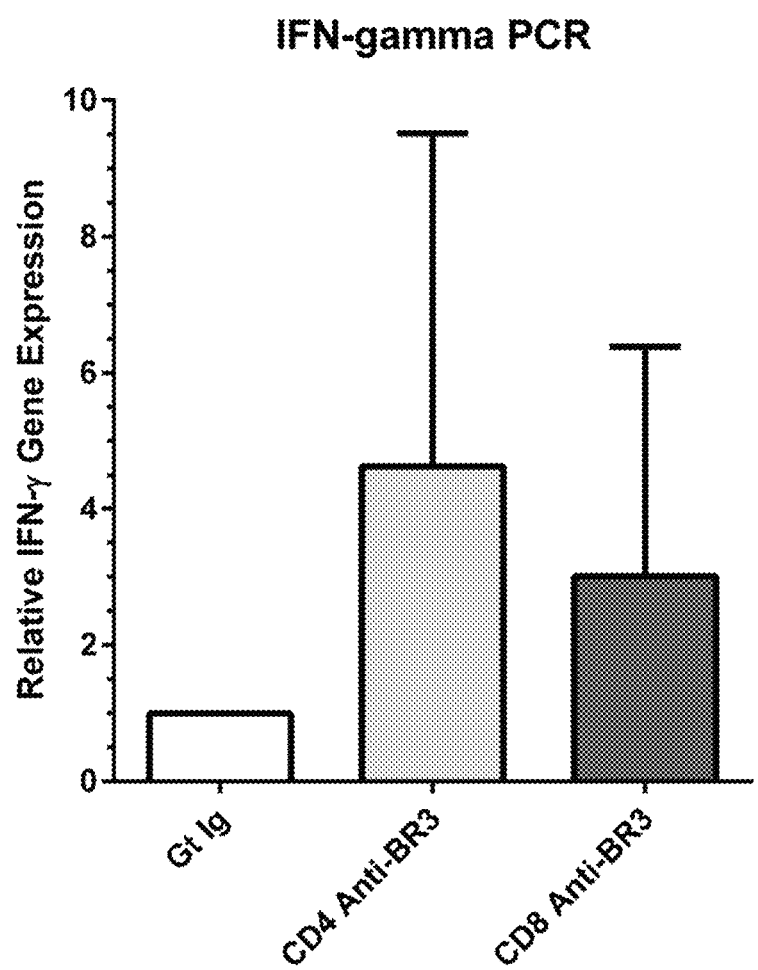
FIGS. 6A-6C shows increased IFN-γ expression in purified CD4+ and CD8+ T cell subsetswith BR3 blockade. (A) Dot plot of intracellular IFN-γ expression with and without anti-BR3. (B) 21 hour ELISA of IFN-γ expression in CD4+ and CD8+ T cells. (C) Semi-quantitative PCR at 21 hour post-activation. Shown is relative gene expression of IFN-γ in CD4+ and CD8+ T cells treated with the goat IgG control or anti-BR3.
Figures 7A, 7B, 7C:
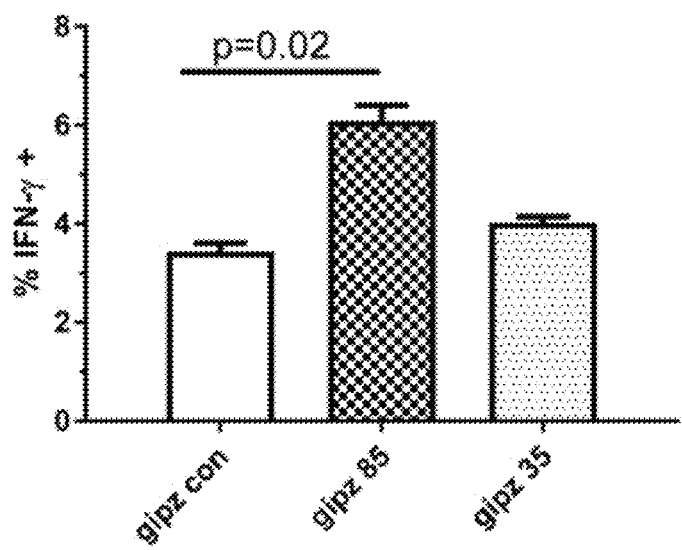
FIGS. 7A-7C shows the inhibition by shRNA increases CD25 and IFN-γ. (A) The use of shRNA down modulates BR3 expression in CD4+ T cells. GIPZ BR3 specific shRNA constructs from Dharmacon, Inc. were used in addition to the GIPZ control vector (B) CD25 expression increases on the cell surface of T cells with shRNA down regulation of BR3. Flow cytometric analysis was performed after an 18 hour rest of T cells after nucleoporation with a subsequent 21 hour activation period. (C) Expression of IFN-γ increases in BR-3 silenced CD4+ T cells. Intracellular flow cytometry was performed after 18 hours of activation with a subsequent 6 hour incubation in the presence of Brefeldin A.

BR3 Antibody Blockade Increases Expression of IFN-γ: We next examined whether anti-BR3 had an effect on IFN-γ, a key cytokine expressed at the onset of T cell activation. As above, purified T cells were incubated with the series of neutralization antibodies and then stimulated with anti-CD3/CD28. IFN-γ expression was then analyzed by semi-quantitative PCR, intracellular flow cytometry, and ELISA. Increases in IFN-γ levels in culture supernatants after 24 hours of activation were 2-5 fold with anti-BR3, depending on the PBL donor (FIG. 6A) and was statistically significant ($p<0.05$). Anti-BCMA and anti-TACI did not increase IFN-γ expression. As shown in FIG. 7B, anti-BR3 increased intracellular IFN-γ protein expression 2-3 fold (see the representative dot plot) for CD4+ and CD8+ subsets (FIG. 6B). PCR analysis demonstrated that IFN-γ mRNA expression also increased in the anti-BR3 treated group compared to the Ig control, 2-10 fold for CD4+ cells and 2-6 fold for CD8+ cells (FIG. 6C). There were several exceptions to this trend since 2 of 6 donors did not show an increase in IFN-g mRNA expression. However, all donors showed an increase in IFN-γ in tissue culture supernatants. These levels were increased further when 2 ng/ml BAFF was added to anti-BR3 cultures.

Silencing of BR3 Gene Expression also Increases anti-CD3/CD28 Mediated T cell Activation: We wanted to examine whether or not T cell activation by the anti-BR3 blocking antibody was an epiphenomenon of the antibody itself. To strengthen the argument that BR3 on CD3/CD28 activated T cells is inhibitory to T cell activation, we examined whether shRNA gene silencing of BR3 on activated T cells would mimic the anti-BR3 antibody in terms of augmented T cell activation.

Three BR3 specific shRNA constructs (Dharmacon, Inc.) as well as the control shRNA GIPZ plasmids were tested. Briefly, purified T cells were transfected via nucleoporation (Amaxa, Inc.), rested for 20 hours, and then activated by plate-bound anti-CD3 and anti-CD28 for 24 hours (see Materials and Methods). Of the BR3 shRNA constructs, two effectively decreased BR3 expression by greater than 70% compared to the control shRNA, as analyzed by flow cytometry (FIG. 7A). Of the two that decreased BR3 expression, only construct 85 increased CD25 expression (FIG. 7B) both for CD4+ and CD8+ cells. Forward scatter of the activated cells transfected with BR3-specific shRNA also increased (data not shown).

We likewise analyzed the BR3 shRNA constructs for IFN-γ expression using intracellular flow cytometry. Transfected T cells were activated for 5 hours in the presence of Brefeldin A. As shown in FIG. 7C, IFN-γ expression increased significantly in the Br3-silenced activated T cells compared to the control shRNA. These data further support the hypothesis that BR3 can inhibit anti-CD3/CD28 T cell activation.

Figure 8A:
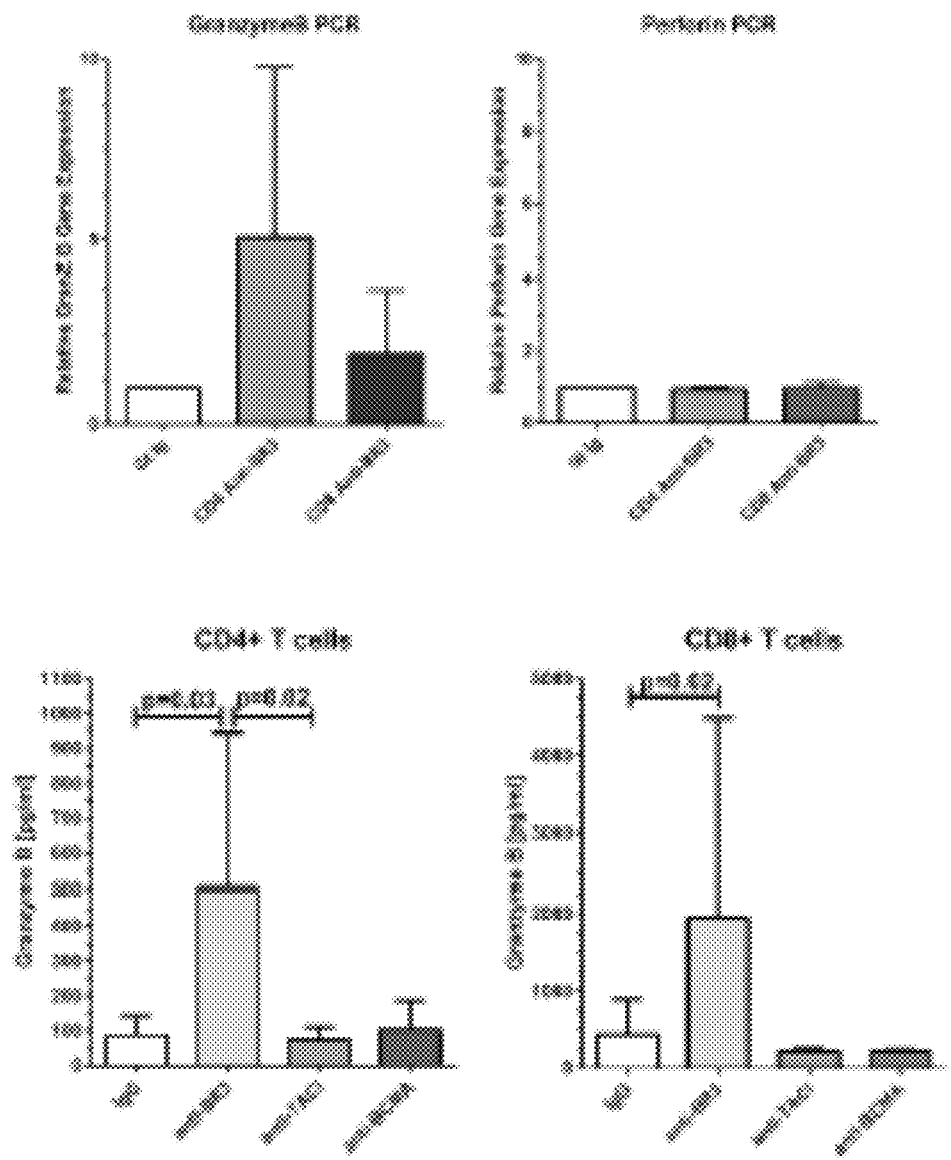
FIGS. 8A-8D demonstrates that anti-BR3 augments T cell cytotoxicity. (A)

Blockade of BR3 Increases Granzyme B Expression and Cytolytic T cell Activation: Since IFN-γ was increased in CD8+ T cells with BR3 blockade, we considered whether factors involved in cytotoxicity were likewise augmented. As such, we looked at the expression of granzyme B and perforin, at the mRNA and protein levels, both for CD4 and CD8 subsets. Perforin expression was not affected by anti-BR3 (FIG. 8A). However, granzyme B levels increased 2-10 fold for CD4+ as well as CD8+ T cells as demonstrated by PCR and ELISA (FIG. 8A).

Figure 8B:
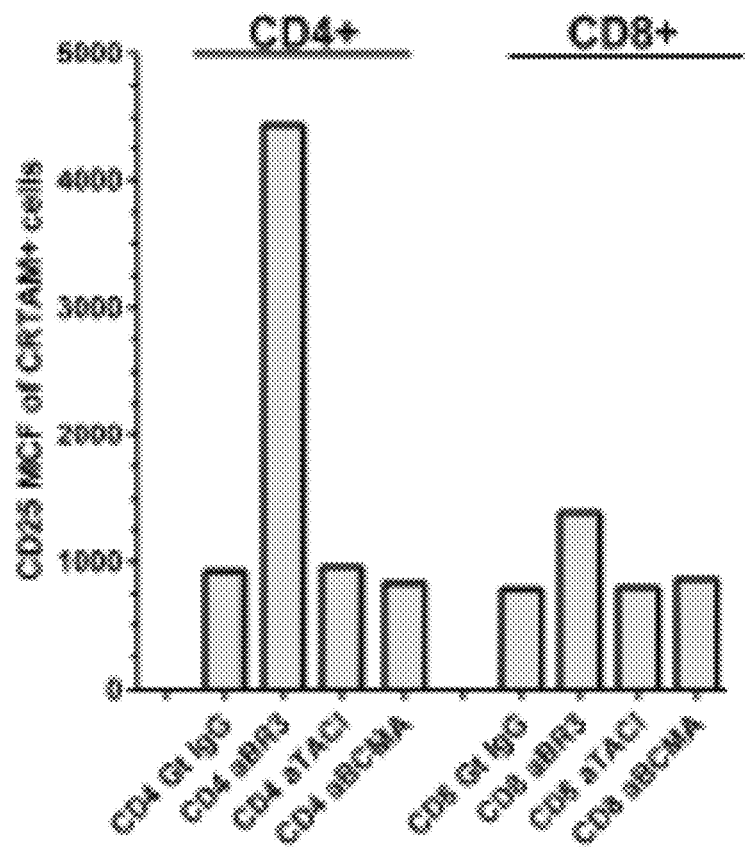

We next used the cytolytic T cell marker CRTAM to assess whether active cytolytic T cells increased activation with BR3 neutralization. As shown in FIG. 8B, both CRTAM+CD4+ and to a lesser extent CRTAM+CD8+ cells significantly increased CD25 expression in the presence of anti-BR3. This suggested that BR3 may augment the cytolytic function of T cells.

To assess whether anti-BR3 could increase the killing function of T cells, we used the melanoma cell line A375 as a target for activated CD4 and CD8 T effector cells. A375 cells are an endothelial derived line that express both HLA Class I and Class II. Purified T effector cells from a healthy donor which were pan-T cell activated with anti-CD3/anti-CD28 were able to kill A375 melanoma tumor cells. Pre-incubation with anti-BR3 with subsequent pan-T cell activation enhanced A375 killing 4 fold in a CFSE-Propidium Iodide assay. After 4 days in culture, the fibroblast-like A375 cells were significantly diminished (FIG. 8D). Together, these data suggest that anti-BR3 can enhance T cell cytotoxicity of both CD4+ and CD8+ cells.

Figure 8C:
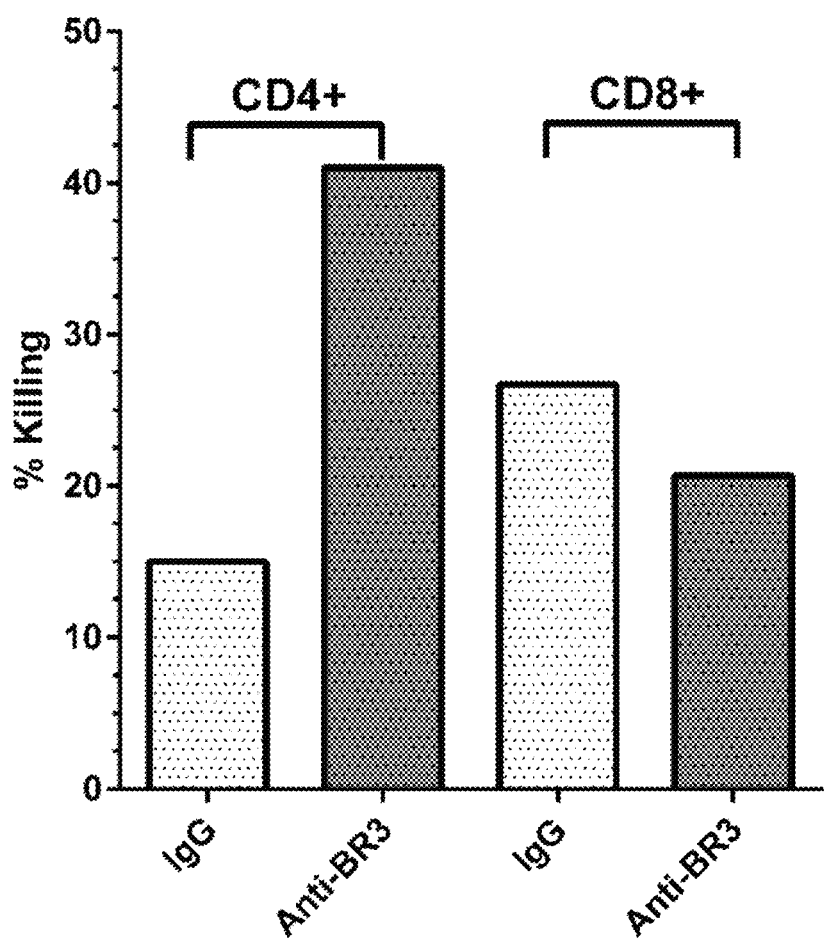
Figure 8D:
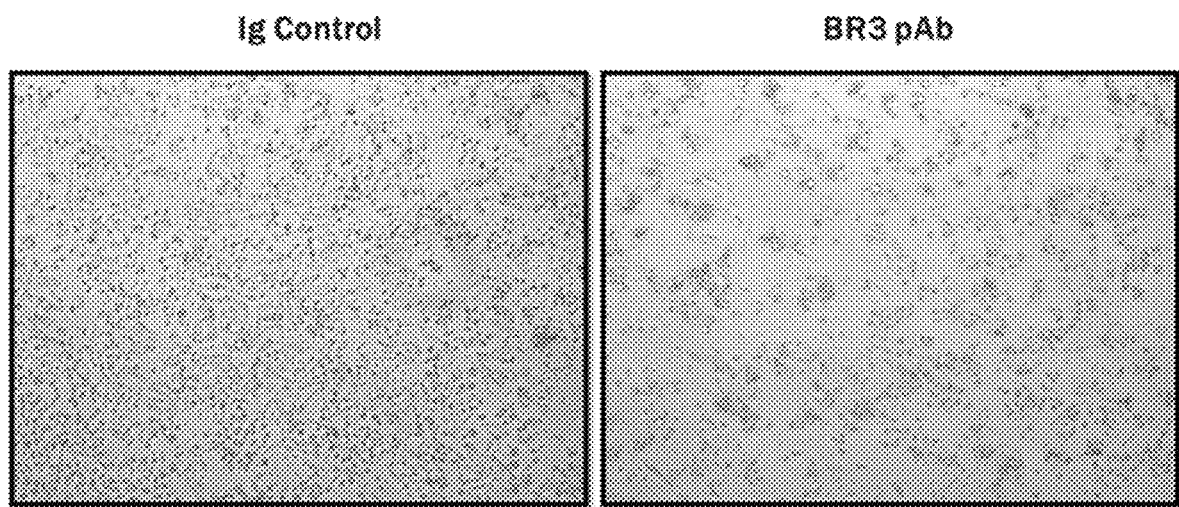
Figure 9:
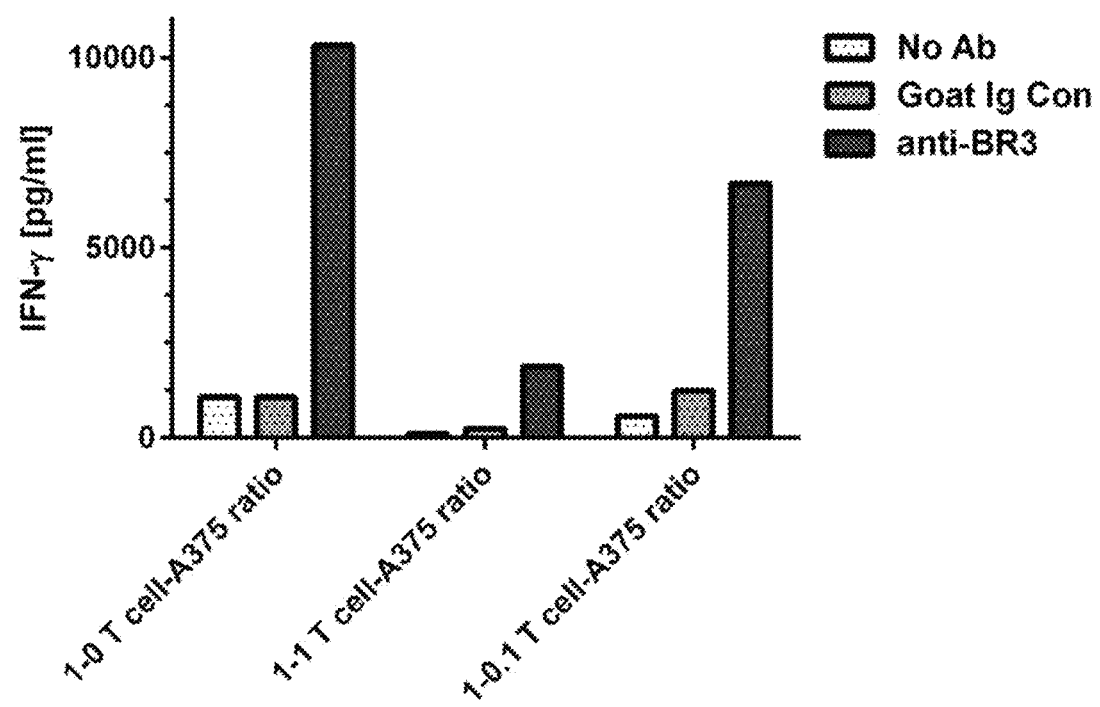
FIG. 9 shows IFN-γ levels in T cell-A375 co-culture supernatants as described in FIG. 8D. T cells were cultured with A375 cells at a 1-0, 1-1, and 1-0.1 ratio with no antibody, the goat IgG control, and anti-BR3. A375 cells suppress T cell activation. Anti-BR3 overcomes A375 mediated suppression of IFN-gamma production.

FIG. 8C depicts the lysis of myeloma line U266 and demonstrates that cytolytic CD4+ T cells can kill more effectively in the presence of anti-BR3. This is important as it demonstrates that the use of anti-BR3 and the reduction in BR3 activity can augment the killing function of CD4+ CTLs and not just the classic CD8+ CTLs. The killing of U266 is a good example of this because in this assay, CD4+ CTLs are likely targeting the class II (HLA-DR) mismatched molecules on U266 B cells. There are likely plenty of tumor antigens presented by class II that CD4+ CTLS can target. Anti-BR3 would be a beneficial therapeutic to significantly augment the activation and killing function of this T cell subset.

Discussion

Data presented herein demonstrates that BAFF-R/BR3 expressed on human CD4 and CD8 T cells can limit anti-CD3/CD28 mediated activation and cytotoxicity. Inhibiting BAFF binding to BR3 or down-modulating its expression augments IFN-γ and granzyme B expression. In addition, neutralization with anti-BR3 promotes the killing of tumor cell line A375 in vitro.

We are cognizant of previous reports which show that the ligand BAFF enhances, not suppresses, CD4+ T cell proliferation. For instance, BAFF co-stimulated TCR activation of both murine and human T cells in the absence of CD28 signaling in several studies. These reports vary from ours in several distinct ways. First, plate-bound BAFF at microgram levels was utilized in activation assays whereas we relied on the membrane-bound and soluble BAFF expressed by the activated T cells themselves. As such, levels of soluble BAFF were at picogram levels, levels that more mimic those in normal human sera. Furthermore, activation and proliferation was measured at 72 hours post-stimulation, much later than the optimal activation period of 24 hours. Finally, these groups did not specifically down-modulate BR3. Instead, BR3 was designated as the BAFF receptor mediating the augmentation of T cell activation/proliferation based on the inexpression of TACI and BCMA. We were able to amplify BCMA-specific mRNA and detect BCMA on the cell surface of activated T cells. In addition, low levels of TACI mRNA were also detected in our activated T cells and TACI was expressed on both CD4 and CD8 cells. As such, specific blockade of BR3 as well as its down-modulation was necessary to determine that BR3 may suppress human T cell activation in vitro.

In studies in vivo, BAFF −/− mice demonstrated modest prolongation of allograft survival in a heart transplant model and certain TH1 responses are enhanced in BAFF and BAFF-R transgenic mice. However, the concept that BAFF only enhances T cell activation is far from definitive since BAFF −/− mice also display normal TH1 responses. Furthermore, in a murine EAE model, BAFF-R deficiency led to increased disease severity. And in clinical trials using anti-BAFF therapeutics for autoimmune diseases such as multiple sclerosis, there have been more than several instances of increased disease severity. Thus, it was important that we reinvestigated the possible dual nature of BAFF's effects on T cells. Considering the body of our data, we propose that BAFF/BR3 suppresses cytotoxic T cell function. To our knowledge, this is the first report addressing the function of BR3 on human cytolytic CD4+ and CD8+ cells.

From a signaling perspective, what sets BR3 apart from TACI and BCMA? All three BAFF receptors signal via the direct and indirect NF-kB pathways but only BR3 has been shown to suppress PKC-δ signaling. It may be possible that PKC-δ, which is suppressed by BR3, is increased with anti-BR3 mediated neutralization. It has been demonstrated that PKC-δ increases lysosomal activity in CTLs. Thus, this may be one possible mode of action for this blocking antibody. Experiments are underway to determine whether PKC-δ signaling is linked to BR3-mediated Tc suppression.

There are many therapeutic implications to this finding. Increased BAFF levels in cancer, autoimmunity, and immune deficiencies may be suppressing CTLs. As such, therapeutic BAFF ligand competitors may, in some instances of autoimmunity and transplantation, neutralize BR3 function to detrimentally increase the activation of auto- and allo-reactive T cells. However, in instances of some cancers and immune deficiencies such as AIDS, blockade of BR3 with ligand competitors or BR3-targeted antibodies could increase CTL function and assist in disease correction.

One clear application for BR3 neutralization is that of ex-vivo Tc lymphocyte activation for CAR-T or TIL based cancer immune therapies. Currently, activation and expansion of chimeric and tumor infiltrating T cells is implemented primarily by stimulating cells with anti-CD3 and anti-CD28 with subsequent IL-2 based expansion. Given our data that demonstrate an increase in expression of the low affinity IL-2 chain CD25, we hypothesize that addition of an anti-BR3 neutralization antibody could enhance the expansion of activated CD4+ and CD8+ CTLs. Experiments to test whether the addition of anti-BR3 to activated T cells generates a more effective tumor-killing product are underway.

REFERENCES

1. Callahan M K, Postow M A, Wolchok J D. 2014. CTLA-4 and PD-1 Pathway Blockade: Combinations in the Clinic. Frontiers in oncology 4:385.
2. Mackay F, Silveira P A, Brink R. 2007. B cells and the BAFF/APRIL axis: fast-forward on autoimmunity and signaling. Curr Opin Immunol 19:327-336.
3. Bossen C, Schneider P. 2006. BAFF, APRIL and their receptors: structure, function and signaling. Semin Immunol 18:263-275.
4. Lesley R, Xu Y, Kalled S L, Hess D M, Schwab S R, Shu H B, Cyster J G. 2004. Reduced competitiveness of autoantigen-engaged B cells due to increased dependence on BAFF. Immunity 20:441-453.
5. Mackay F, Schneider P. 2009. Cracking the BAFF code. Nat Rev Immunol 9:491-502.
6. Bloom D, Chang Z, Pauly K, Kwun J, Fechner J, Hayes C, Samaniego M, Knechtle S. 2009. BAFF is increased in renal transplant patients following treatment with alemtuzumab. Am J Transplant 9:1835-1845.
7. Davidson A. 2010. Targeting BAFF in autoimmunity. Curr Opin Immunol 22:732-739.
8. Ryan M C, Grewal I S. 2009. Targeting of BAFF and APRIL for autoimmunity and oncology. Adv Exp Med Biol 647:52-63.
9. Vincent F B, Saulep-Easton D, Figgett W A, Fairfax K A, Mackay F. 2013. The BAFF/APRIL system: emerging functions beyond B cell biology and autoimmunity. Cytokine Growth Factor Rev 24:203-215.
10. Rickert R C, Jellusova J, Miletic A V. 2011. Signaling by the tumor necrosis factor receptor superfamily in B-cell biology and disease. Immunol Rev 244:115-133.
11. Mackay F, Leung H. 2006. The role of the BAFF/APRIL system on T cell function. Semin Immunol 18:284-289.
12. Ye Q, Wang L, Wells A D, Tao R, Han R, Davidson A, Scott M L, Hancock W W. 2004. BAFF binding to T cell-expressed BAFF-R costimulates T cell proliferation and alloresponses. Eur J Immunol 34:2750-2759.
13. Ng L G, Sutherland A P, Newton R, Qian F, Cachero T G, Scott M L, Thompson J S, Wheway J, Chtanova T, Groom J, Sutton I J, Xin C, Tangye S G, Kalled S L, Mackay F, Mackay C R. 2004. B cell-activating factor belonging to the TNF family (BAFF)-R is the principal BAFF receptor facilitating BAFF costimulation of circulating T and B cells. Journal of immunology (Baltimore, Md.: 1950) 173:807-817.
14. Sutherland A P, Ng L G, Fletcher C A, Shum B, Newton R A, Grey S T, Rolph M S, Mackay F, Mackay C R. 2005. BAFF augments certain Th1-associated inflammatory responses. Journal of immunology (Baltimore, Md.: 1950) 174:5537-5544.
15. Diaz-de-Durana Y, Mantchev G T, Bram R J, Franco A. 2006. TACI-BLyS signaling via B-cell-dendritic cell cooperation is required for naive CD8+ T-cell priming in vivo. Blood 107:594-601.
16. Schiemann B, Gommerman J L, Vora K, Cachero T G, Shulga-Morskaya S, Dobles M, Frew E, Scott M L. 2001. An essential role for BAFF in the normal development of B cells through a BCMA-independent pathway. Science (New York, N.Y.) 293:2111-2114.

17. Kim S S, Richman D P, Zamvil S S, Agius M A. 2011. Accelerated central nervous system autoimmunity in BAFF-receptor-deficient mice. J Neurol Sci 306:9-15.
18. Corkum C P, Ings D P, Burgess C, Karwowska S, Kroll W, Michalak T I. 2015. Immune cell subsets and their gene expression profiles from human PBMC isolated by Vacutainer Cell Preparation Tube (CPT™) and standard density gradient. BMC Immunol. August 26; 16:48.
19. Bloom D D, Centanni J M, Bhatia N, Emler C A, Drier D, Leverson G E, McKenna D H, Jr., Gee A P, Lindblad R, Hei D J, Hematti P. 2015. A reproducible immunopotency assay to measure mesenchymal stromal cell-mediated T-cell suppression. Cytotherapy 17:140-151.
20. Ward-Kavanagh L K, Lin W W, Sedy J R, Ware C F. 2016. The TNF Receptor Superfamily in Co-stimulating and Co-inhibitory Responses. Immunity 44:1005-1019.
21. Figueroa J A, Reidy A, Mirandola L, Trotter K, Suvorava N, Figueroa A, Konala V, Aulakh A, Littlefield L, Grizzi F, Rahman R L, Jenkins M R, Musgrove B, Radhi S, D'Cunha N, D'Cunha L N, Hermonat P L, Cobos E, Chiriva-Internati M. 2015. Chimeric antigen receptor engineering: a right step in the evolution of adoptive cellular immunotherapy. International reviews of immunology 34:154-187.
22. Faurschou M, Jayne D R. 2014. Anti-B cell antibody therapies for inflammatory rheumatic diseases. Annu Rev Med 65:263-278.
23. Patino-Lopez G, Hevezi P, Lee J, Willhite D, Verge G M, Lechner S M, Ortiz-Navarrete V, Zlotnik A. 2006. Human class-I restricted T cell associated molecule is highly expressed in the cerebellum and is a marker for activated NKT and CD8+ T lymphocytes. Journal of neuroimmunology 171:145-155.
24. Takeuchi A, Badr Mel S, Miyauchi K, Ishihara C, Onishi R, Guo Z, Sasaki Y, Ike H, Takumi A, Tsuji N M, Murakami Y, Katakai T, Kubo M, Saito T. 2016. CRTAM determines the CD4+ cytotoxic T lymphocyte lineage. The Journal of experimental medicine 213:123-138.
25. Ma J S, Haydar T F, Radoja S. 2008. Protein kinase C delta localizes to secretory lysosomes in CD8+ CTL and directly mediates TCR signals leading to granule exocytosis-mediated cytotoxicity. Journal of immunology (Baltimore, Md.: 1950) 181:4716-4722.
26. Restifo N P, Dudley M E, Rosenberg S A. 2012. Adoptive immunotherapy for cancer: harnessing the T cell response. Nature reviews. Immunology 12:269-281.
27. Khalil D N, Smith E L, Brentjens R J, Wolchok J D. 2016. The future of cancer treatment: immunomodulation, CARs and combination immunotherapy. Nature reviews. Clinical oncology 13:273-290.
28. Fesnak A D, June C H, Levine B L. 2016. Engineered T cells: the promise and challenges of cancer immunotherapy. Nature reviews. Cancer 16:566-581.
29. Ninomiya S, Narala N, Huye L, Yagyu S, Savoldo B, Dotti G, Heslop H E, Brenner M K, Rooney C M, Ramos C A. 2015. Tumor indoleamine 2,3-dioxygenase (IDO) inhibits CD19-CAR T cells and is downregulated by lymphodepleting drugs. Blood 125:3905-3916.
30. Frigault M J, Lee J, Basil M C, Carpenito C, Motohashi S, Scholler J, Kawalekar O U, Guedan S, McGettigan S E, Posey A D, Jr., Ang S, Cooper L J, Platt J M, Johnson F B, Paulos C M, Zhao Y, Kalos M, Milone M C, June C H. 2015. Identification of chimeric antigen receptors that mediate constitutive or inducible proliferation of T cells. Cancer immunology research 3:356-367.

We claim:
1. A method of preparing a population of T cells, the method comprising
   (a) reducing BAFF-R receptor activity in the T cells; and
   (b) culturing the T cells of (a) for about 3 to about 14 days in the presence of an anti-CD3 antibody and an anti-CD28 antibody under conditions appropriate for activating cytotoxic T cells,
   wherein the reducing and culturing activates and induces proliferation of activated T cells to yield a population comprising activated T cells in sufficient numbers for use in therapy.
2. The method of claim 1, wherein the T cells are selected from the group consisting of a leukocyte-containing cell mixture and a purified T cell population.
3. The method of claim 2, wherein the leukocyte-containing cell mixture or purified T cell population is obtained from apheresis of peripheral blood of a human subject.
4. The method of claim 2, wherein the leukocyte-containing cell mixture or purified T cell population is obtained from peripheral blood mononuclear cells of a human subject.
5. The method of claim 1, wherein the population comprises at least one of activated $CD4^+$ T cells and $CD8^+$ T cells.
6. The method of claim 1, wherein cytotoxic $CD8^+$ T cells are preferentially expanded from the activated T cell population.
7. The method of claim 1, wherein the method of step (a) is selected from the group consisting of:
   (i) culturing T cells in the presence of a BAFF-R antagonist; and
   (ii) contacting T cells with a BAFF-R specific shRNA.
8. The method of claim 7, wherein the BAFF-R antagonist is a neutralizing BAFF-R antibody.
9. A method of claim 1 additionally comprising the step of:
   (c) providing in the T cells a chimeric antigen receptor, to generate a population of activated T cells comprising the chimeric antigen receptor.
10. The method of claim 9, wherein the providing step (c) comprises a method step selected from the group consisting of:
    (i) introducing the chimeric antigen receptor into the T cells; and
    (ii) transfecting a nucleic acid vector encoding the chimeric antigen receptor into the T cells whereby the T cells express the chimeric antigen receptor.
11. The method of claim 9, wherein the reducing step (a) comprises a method step selected from the group consisting of:
    (i) culturing T cells in the presence of a BAFF-R antagonist; and
    (ii) contacting T cells with a BAFF-R specific shRNA.
12. The method of claim 11, wherein the BAFF-R antagonist is a neutralizing BAFF-R antibody.
13. A method of preparing a population of T cells, the method comprising
    (a) reducing BAFF-R receptor activity in the T cells; and
    (b) culturing the T cells of (a) for about 3 to about 14 days in the presence of an anti-CD3 antibody, or a CD3-binding fragment thereof, and an anti-CD28 antibody, or a CD28-binding fragment thereof, under conditions appropriate for activating cytotoxic T cells, wherein the reducing and culturing activates and induces proliferation of activated T cells to yield a population comprising activated T cells in sufficient numbers for use in therapy.

14. The method of claim 13, wherein the anti-CD3 antibody is an anti-CD3ε antibody.

15. The method of claim 14, wherein the anti-CD3ε antibody is selected from the group consisting of clone UCHT1 and clone OKT3.

16. The method of claim 13, wherein the anti-CD28 antibody is selected from the group consisting of clone 37407 and clone 9.3.

17. The method of claim 13, wherein the anti-CD3 and anti-CD28 antibodies are attached to a substrate.

18. The method of claim 17, wherein the substrate is a plate or a bead.

19. The method of claim 13, wherein the T cells are selected from the group consisting of a leukocyte-containing cell mixture and a purified T cell population.

20. The method of claim 19, wherein the leukocyte-containing cell mixture or purified T cell population is obtained from apheresis of peripheral blood of a human subject.

21. The method of claim 13, wherein the population comprises at least one of activated $CD4^+$ T cells and $CD8^+$ T cells.

22. The method of claim 13, wherein the method of step (a) is selected from the group consisting of:

(i) culturing T cells in the presence of a BAFF-R antagonist; and (ii) contacting T cells with a BAFF-R specific shRNA.

23. The method of claim 22, wherein the BAFF-R antagonist is a neutralizing BAFF-R antibody.

24. A method of claim 13 additionally comprising the step of:

(c) providing in the T cells a chimeric antigen receptor, to generate a population of activated T cells comprising the chimeric antigen receptor.

25. The method of claim 24, wherein the providing step (c) comprises a method step selected from the group consisting of:

(i) introducing the chimeric antigen receptor into the T cells; and (ii) transfecting a nucleic acid vector encoding the chimeric antigen receptor into the T cells whereby the T cells express the chimeric antigen receptor.

26. The method of claim 24, wherein the reducing step (a) comprises a method step selected from the group consisting of:

(i) culturing T cells in the presence of a BAFF-R antagonist; and (ii) contacting T cells with a BAFF-R specific shRNA.

27. The method of claim 26, wherein the BAFF-R antagonist is a neutralizing BAFF-R antibody.

* * * * *